United States Patent
Nomura et al.

(10) Patent No.: US 8,101,771 B2
(45) Date of Patent: Jan. 24, 2012

(54) TRIAZOLE DERIVATIVE, AND LIGHT-EMITTING ELEMENT, LIGHT-EMITTING DEVICE, AND ELECTRONIC DEVICE USING TRIAZOLE DERIVATIVE

(75) Inventors: Hiroko Nomura, Fukuoka (JP); Sachiko Kawakami, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 220 days.

(21) Appl. No.: 12/550,537

(22) Filed: Aug. 31, 2009

(65) Prior Publication Data
US 2010/0079066 A1 Apr. 1, 2010

(30) Foreign Application Priority Data

Sep. 1, 2008 (JP) .................. 2008-223655

(51) Int. Cl.
*C07D 401/10* (2006.01)
*B32B 9/00* (2006.01)
*H01J 1/62* (2006.01)

(52) U.S. Cl. .............. 546/272.4; 546/268.1; 428/690; 428/917; 313/504; 313/506; 315/169.3

(58) Field of Classification Search .......... 546/268.1, 546/272.4; 428/690, 917; 313/504, 506; 315/169.3
See application file for complete search history.

(56) References Cited

U.S. PATENT DOCUMENTS

| | | | | |
|---|---|---|---|---|
| 7,723,722 B2* | 5/2010 | Kawakami et al. | ............. | 257/40 |
| 7,796,240 B2* | 9/2010 | Nomura et al. | ................. | 356/32 |
| 7,838,128 B2* | 11/2010 | Kawakami et al. | ........... | 428/690 |
| 7,875,879 B2* | 1/2011 | Suzuki et al. | ................... | 257/40 |
| 7,901,792 B2* | 3/2011 | Egawa et al. | ................. | 428/690 |
| 7,911,135 B2* | 3/2011 | Sakata et al. | ................... | 313/506 |
| 7,927,720 B2* | 4/2011 | Nomura et al. | ............... | 428/690 |
| 2007/0216292 A1 | 9/2007 | Seo et al. | | |
| 2007/0262693 A1 | 11/2007 | Seo et al. | | |
| 2008/0135835 A1 | 6/2008 | Seo et al. | | |
| 2008/0286607 A1 | 11/2008 | Nomura et al. | | |
| 2008/0296561 A1 | 12/2008 | Nomura et al. | | |
| 2009/0153041 A1 | 6/2009 | Kawakami et al. | | |
| 2009/0160324 A1 | 6/2009 | Nomura et al. | | |

FOREIGN PATENT DOCUMENTS

JP 2002-352957 12/2002

* cited by examiner

*Primary Examiner* — Golam M M Shameem
(74) *Attorney, Agent, or Firm* — Husch Blackwell LLP

(57) ABSTRACT

A novel triazole derivative which has a large energy gap and can be used for electron-transporting layer of a light-emitting element or as a host material. In addition, a light-emitting element which has higher emission efficiency by using the novel triazole derivative. Furthermore, a low power consumption light-emitting device and electronic device.

A triazole derivative having a structure represented by the formula (G1).

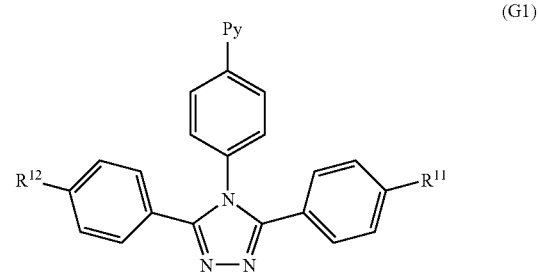

(G1)

In the formula, Py represents a pyridyl group. $R^{11}$ and $R^{12}$ each represent any of hydrogen, an alkyl group having 1 to 4 carbon atoms, an alkoxy group having 1 to 4 carbon atoms, or a phenyl group.

21 Claims, 14 Drawing Sheets

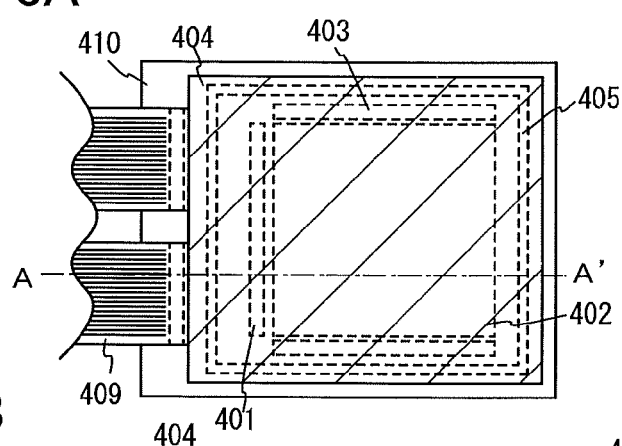
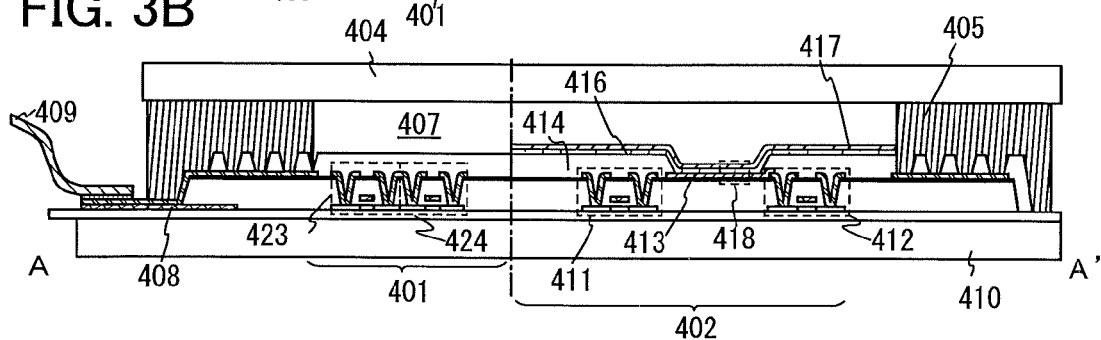

TRIAZOLE DERIVATIVE, AND LIGHT-EMITTING ELEMENT, LIGHT-EMITTING DEVICE, AND ELECTRONIC DEVICE USING TRIAZOLE DERIVATIVE

BACKGROUND OF THE INVENTION

1. Field of the Invention

The present invention relates to a triazole derivative, in particular, a triphenyl triazole derivative having a pyridyl group. Further, an embodiment of the present invention relates to a light-emitting element, a light-emitting device, an electronic device, and lighting equipment in each of which the triphenyl triazole derivative having a pyridyl group is used.

2. Description of the Related Art

A light-emitting element in which an organic compound is used as a light-emitting substance has a simple structure in which only a light-emitting layer containing an organic compound that is a light-emitting substance is provided between electrodes, and has attracted attention as a next-generation flat panel display element because of its characteristics such as thinness, lightweight, high response speed, and low direct current voltage driving. In addition, a display in which this light-emitting element is used is excellent in contrast and image quality, and has wide viewing angle.

The emission mechanism of a light-emitting element in which an organic compound is used as a light-emitting substance is of a carrier injection type. In other words, when voltage is applied with a light-emitting layer interposed between electrodes, electrons and holes injected from the electrodes are recombined to make the light-emitting substance excited, and light is emitted when the excited state returns to a ground state. As in the case of photoexcitation, the types of the excited state include a singlet excited state (S*) and a triplet excited state (T*). The statistical generation ratio thereof in a light-emitting element is considered to be S*:T*=1:3.

On the other hand, when a compound which converts a triplet excited state into light emission (hereinafter such a compound is referred to as a "phosphorescent compound") is used, internal quantum efficiency can be theoretically 75% to 100%. In other words, emission efficiency that is 3 times to 4 times as much as that of a fluorescence compound can be achieved. For those reasons, in order to achieve a highly efficient light-emitting element, a light-emitting element in which a phosphorescent compound is used has been actively developed recently (for example, see Patent Document 1).

In the case where a light-emitting layer of a light-emitting element is formed using a phosphorescent compound, the light-emitting layer is often formed so that the phosphorescent compound is dispersed in a matrix formed of another substance for suppression of concentration quenching of the phosphorescent compound or quenching due to triplet-triplet annihilation (T-T annihilation). In the above case, a substance which serves as a matrix is referred to as a host material and a substance, like a phosphorescent compound, which is dispersed in a matrix is referred to as a guest material.

In the case where a phosphorescent compound is used as a guest material, a host material is required to have higher triplet excitation energy (a difference in energy between a ground state and a triplet excited state) than the phosphorescent compound.

[Citation List]
[Patent Document 1]
Japanese Published Patent Application No. 2002-352957

However, as for a light-emitting element in which a phosphorescent compound is used as a light-emitting substance, there is a problem in that current efficiency of a light-emitting element which emits blue light is lower than that of a light-emitting element which emits light ranging from red to green.

A phosphorescent compound which emits blue light has a large energy gap. Therefore, a host material which disperses the phosphorescent compound to form a light-emitting layer and a substance which is used for a carrier-transporting layer in contact with a light-emitting region of the light-emitting layer need to have a larger energy gap.

If a material whose energy gap is not large enough is used as a host material of a light-emitting layer or a material for a layer in contact with a light-emitting region, the energy of excitons moves to the material, which causes decrease in emission efficiency of the light-emitting element.

It is an object of an embodiment of the present invention to provide a novel triazole derivative which has a large energy gap and can be used for an electron-transporting layer of a light-emitting element or as a host material. It is another object thereof to provide a light-emitting element having high emission efficiency. It is still another object thereof to provide a low power consumption light-emitting device, electronic device, and lighting equipment.

SUMMARY OF THE INVENTION

The present inventors found out that, after their diligent study for achieving the above objects, a triazole derivative represented by the following general formula (G1) can be used for an electron-transporting layer of a light-emitting element or as a host material.

[Chemical formula 1]

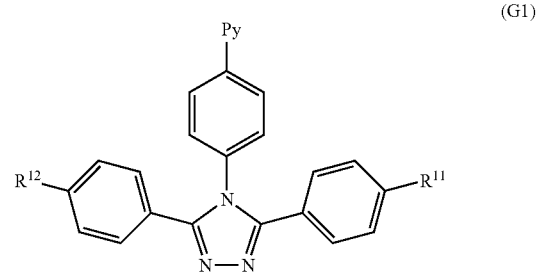

(G1)

In the formula, Py represents any of a 2-pyridyl group, a 3-pyridyl group, or a 4-pyridyl group. $R^{11}$ and $R^{12}$ each represent any of hydrogen, an alkyl group having 1 to 4 carbon atoms, an alkoxy group having 1 to 4 carbon atoms, or a phenyl group.

Further, in the triazole derivative represented by the above general formula (G1), $R^{11}$ and $R^{12}$ each preferably, represent hydrogen for the sake of easy synthesis. In that case, the triazole derivative of an embodiment of the present invention is represented by the following general formula (G2). Therefore, a preferable mode of the present invention is a triazole derivative represented by the following general formula (G2).

[Chemical Formula 2]

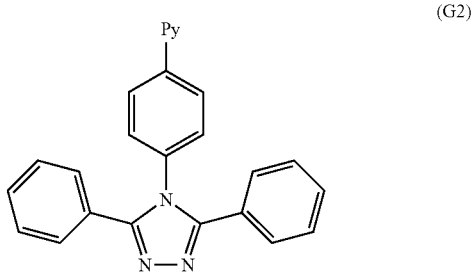

(G2)

In the formula, Py represents a 2-pyridyl group, a 3-pyridyl group, or a 4-pyridyl group. Further, in the triazole derivative represented by the above general formula (G2), a 3-pyridyl group, that is, a pyridyl group is preferably bonded to a phenyl group at the meta position especially for the sake of an excellent electron-transporting property. In that case, the triazole derivative of an embodiment of the present invention is represented by the following structural formula (1). Therefore, a preferable mode of the present invention is a triazole derivative represented by the following structural formula (1).

[Chemical Formula 3]

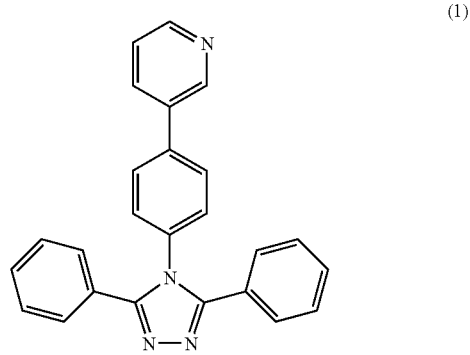

(1)

The triazole derivative of an embodiment of the present invention has a large energy gap, and therefore is useful as a host material of a phosphorescent compound which exhibits blue light emission. In particular, light emission with high efficiency can be obtained with use of the triazole derivative of an embodiment of the present invention, even in the case where a substance is used which emits phosphorescence which exhibits light emission of a short wavelength, the light emission peak wavelength of which is greater than or equal to 400 nm and less than or equal to 500 nm.

Moreover, the triazole derivative of an embodiment of the present invention has an excellent electron-transporting property.

Thus, according to an embodiment of the present invention, a light-emitting element includes, between a pair of electrodes, at least one of the triazole derivatives represented by the above general formulae (G1) and (G2) and structural formula (1).

In addition, according to an embodiment of the present invention, a light-emitting element includes, between a pair of electrodes, a light-emitting layer containing any of the triazole derivatives represented by the above general formulae (G1) and (G2) and structural formula (1) and a substance which emits phosphorescence.

The triazole derivative of an embodiment of the present invention has difficulty in transporting holes, and therefore can be used for a hole-blocking layer. Holes which fail to be recombined in the light-emitting layer can be prevented from running to the cathode side, and not only the emission efficiency of the light-emitting element but also the reliability thereof can be increased.

Thus, according to an embodiment of the present invention, a light-emitting element, which includes, between a cathode and an anode, a light-emitting layer containing a light-emitting substance, includes, between the light-emitting layer and the cathode, a layer formed of any of the triazole derivatives represented by the above general formulae (G1) and (G2) and structural formula (1) so as to be in contact with the light-emitting layer.

Further, according to an embodiment of the present invention, in the light-emitting element which includes, between the cathode and the anode, the light-emitting layer containing any of the triazole derivatives represented by the above general formulae (G1) and (G2) and structural formula (1) and a substance which emits phosphorescence, the layer formed of any of the triazole derivatives represented by the above general formulae (G1) and (G2) and structural formula (1) is provided in contact with the light-emitting layer between the light-emitting layer and the cathode.

Blue-light emission having high emission efficiency can be realized with the thus obtained light-emitting element of an embodiment of the present invention; therefore, a light-emitting device (an image display device or a light-emitting device) in which the light-emitting element is used can also realize low power consumption. Thus, an embodiment of the present invention includes, in its category, light-emitting devices, electronic devices, or lighting equipment in each of which the light-emitting element is used.

A light-emitting device of an embodiment of the present invention includes, between a pair of electrodes, a light-emitting element including a layer in which a light-emitting substance is dispersed in the triazole derivative of an embodiment of the present invention and a control unit for controlling light emission of the light-emitting element. Note that the light-emitting device in this specification includes, in its category, an image display device or a light-emitting device in which a light-emitting element is used. Further, the light-emitting device of an embodiment of the present invention includes, in its category, a module including a substrate provided with a light-emitting element attached with a connector, for example, a tape automated bonding (TAB) tape such as an anisotropic conductive film or a tape carrier package (TCP); a module in which a printed wiring board is provided at an end of the connector; or a module in which an integrated circuit (IC) is directly mounted on a substrate, provided with a light-emitting element, by a chip on glass (COG) method.

The electronic device of an embodiment of the present invention includes a display portion which includes the above light-emitting element and the control unit for controlling light emission of the light-emitting element.

The triazole derivative of an embodiment of the present invention has a large energy gap. In addition, a light-emitting element having high emission efficiency can be obtained with use of the triazole derivative of an embodiment of the present invention. Moreover, a low power consumption light-emitting device, electronic device, and lighting equipment can be obtained.

BRIEF DESCRIPTION OF THE DRAWINGS

In the accompanying drawings:

FIGS. 3A and 3B illustrate a light-emitting device according to Embodiment;

DETAILED DESCRIPTION OF THE INVENTION

Figure 1:
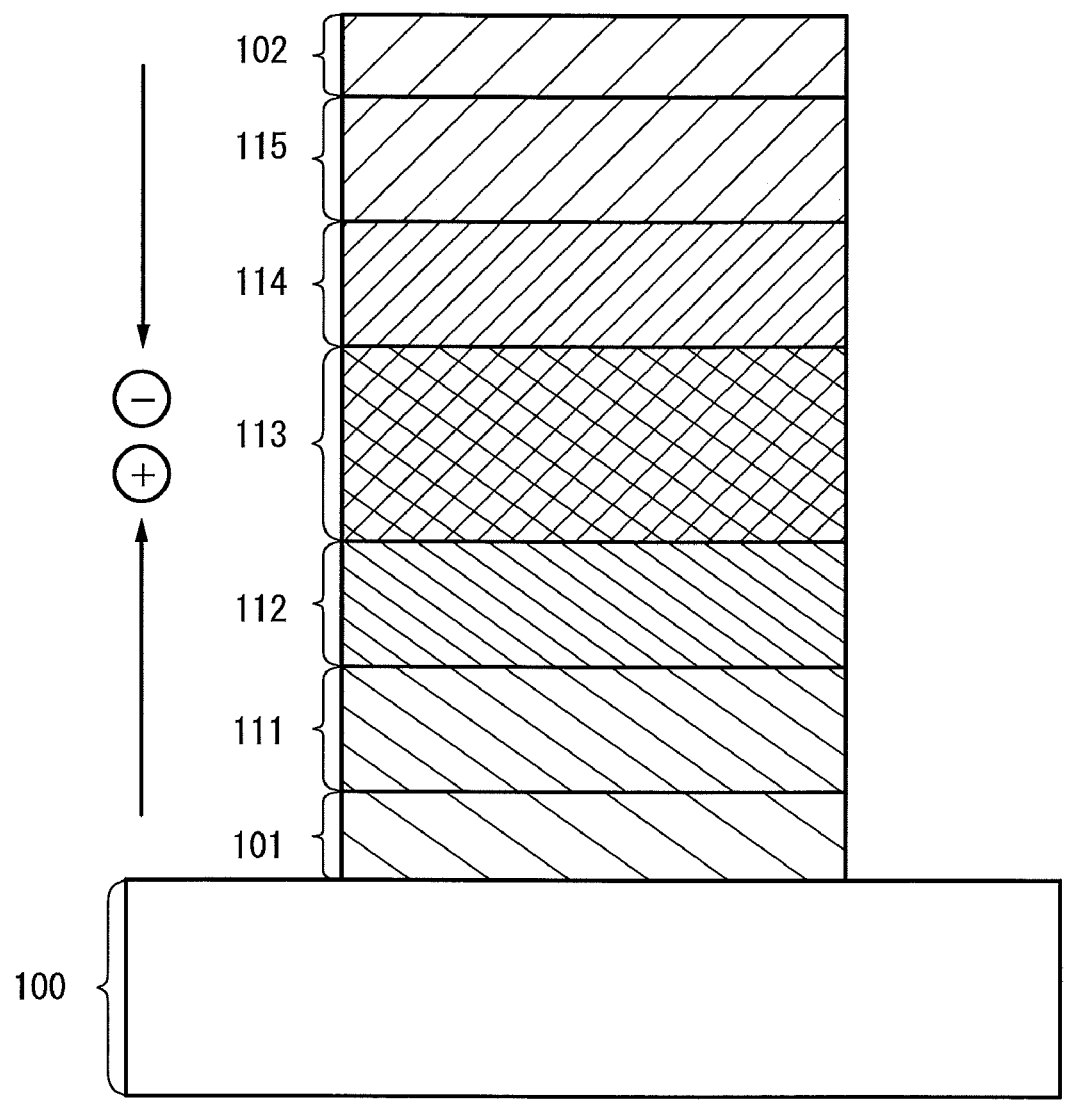
FIG. 1 illustrates a light-emitting element according to Embodiment.

Hereinafter, Embodiments and Examples of the present invention will be described with reference to the accompanying drawings. Note that it is easily understood by those skilled in the art that the present invention can be carried out in many different modes, and the modes and details disclosed herein can be modified in various ways without departing from the spirit and scope of the present invention. Therefore, the present invention should not be construed as being limited to the description below of the embodiments and examples.

Embodiment 1

In Embodiment 1, a triazole derivative of an embodiment of the present invention will be described. The triazole derivative of an embodiment of the present invention has a pyridyl group which has an excellent electron-transporting property in a triazole skeleton which has a high electron-transporting property and high triplet energy.

Specifically, the triazole derivative of an embodiment of the present invention is a 1,2,4-triazole derivative in which a phenyl group is bonded to each of the 3-position and the 5-position and a 4-(pyridyl)phenyl group is bonded to the 4-position. In other words, the triazole derivative of an embodiment of the present invention is a triazole derivative represented by the general formula (G1).

[Chemical Formula 4]

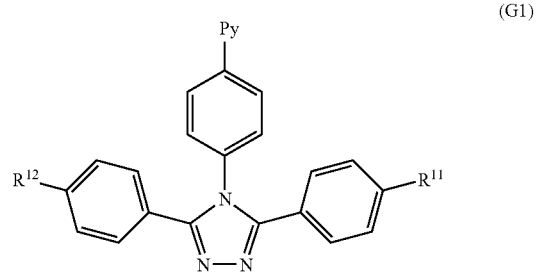

(G1)

In the formula, Py represents a 2-pyridyl group, a 3-pyridyl group, or a 4-pyridyl group. $R^{11}$ and $R^{12}$ each represent any of hydrogen, an alkyl group having 1 to 4 carbon atoms, an alkoxy group having 1 to 4 carbon atoms, or a phenyl group.

In the general formula (G1), $R^{11}$ and $R^{12}$ each preferably represent unsubstituted phenyl group for the sake of easy synthesis. In other words, a triazole derivative represented by the general formula (G2) is preferable.

[Chemical Formula 5]

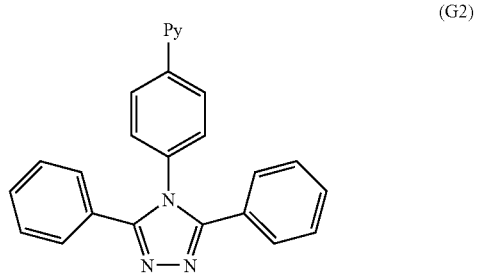

(G2)

In the formula, Py represents a 2-pyridyl group, a 3-pyridyl group, or a 4-pyridyl group.

In the general formula (G2), a pyridyl group is preferably bonded to a 3-pyridyl group, that is, a phenyl group at the meta position especially for the sake of an excellent electron-transporting property. In other words, a triazole derivative represented by the structural formula (1) is preferable.

[Chemical Formula 6]

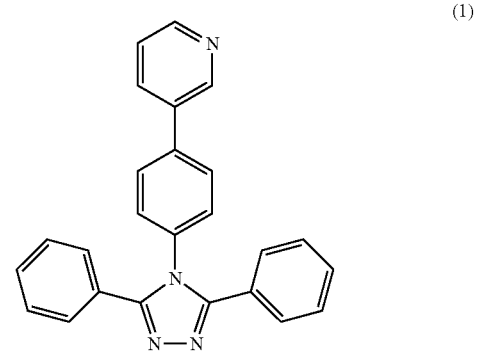

(1)

A variety of reactions can be applied to a synthesis method of the triazole derivative of an embodiment of the present invention. For example, by synthesis reactions described below, the triazole derivative of an embodiment of the present invention can be synthesized. Note that the synthesis method of the triazole derivative of an embodiment of the present invention is not limited to the synthesis method described below.

<Synthesis Method of the Triazole Derivative Represented by the General Formula (G1)>

The triazole derivative represented by the general formula (G1) can be synthesized in such a manner that a halogenated triazole derivative synthesized from ester of aryl carboxylic acid and a compound obtained by substitution of boronic acid of pyridine or a compound of pyridine with organoboron are coupled by Suzuki-Miyaura Coupling.

First, a synthesis scheme of a halogenated triazole derivative (TAZ-2) is described in (a-1).

[Chemical Formula 7]

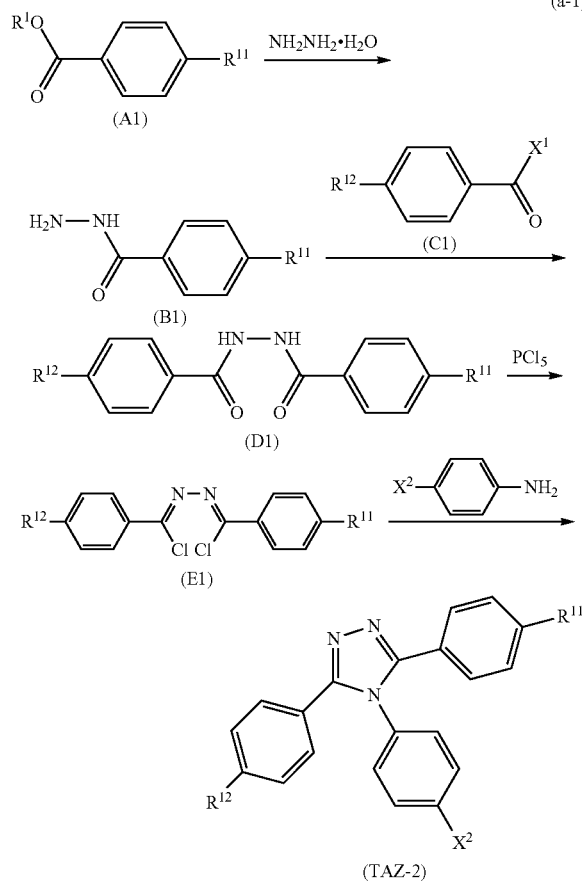

In the formula, $R^1$ represents an alkyl group. $R^{11}$ and $R^{12}$ each represent any of hydrogen, an alkyl group having 1 to 4 carbon atoms, an alkoxyl group having 1 to 4 carbon atoms, or a phenyl group. In addition, $X^1$ and $X^2$ each represent a halogen group.

First, ester of aryl carboxylic acid (A1) is reacted with hydrazine to synthesize halogenated aryl hydrazide (B1). Then, the halogenated aryl hydrazide (B1) is reacted with aryl carboxylic acid halide (C1) to obtain a diacyl hydrazine derivative (D1). Then, the diacyl hydrazine derivative (D1) is reacted with phosphorus pentachloride to obtain a hydrazone derivative (E1). Furthermore, the hydrazone derivative (E1) is reacted with halogenated arylamine to form a 1,2,4-triazole ring. Accordingly, the halogenated triazole derivative (TAZ-2) is obtained. In the above scheme (a-1), $X^1$ is preferably a chloro group and $X^2$ is preferably a bromo group or an iodine group. Note that as a method for synthesizing the halogenated triazole derivative (TAZ-2), other known methods can also be used without limitation to the above scheme (a-1).

Next, a synthesis scheme (a-2) of a triazole derivative (G1) from the halogenated triazole derivative (TAZ-2) is described below.

[Chemical Formula 8]

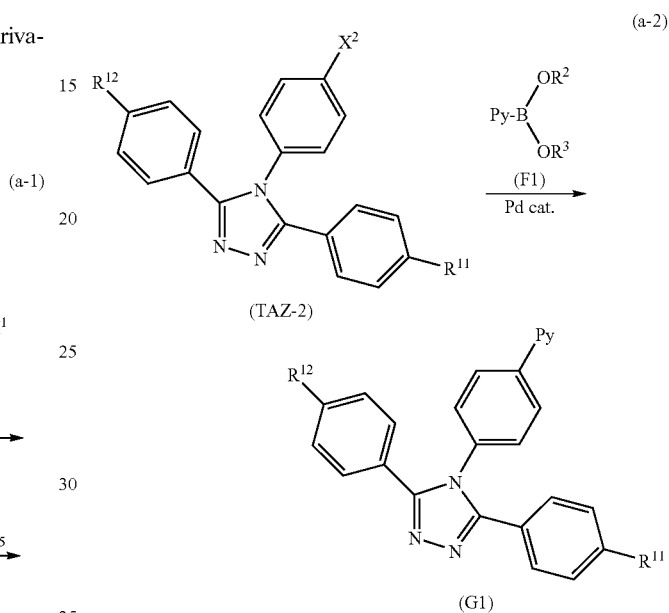

In the formula, $R^2$ and $R^3$ each represent hydrogen or an alkyl group. In addition, $R^2$ and $R^3$ may be bound to each other to form a ring. $X^2$ represents a halogen group or a triflate group. $R^{11}$ and $R^{12}$ each represent any of hydrogen, an alkyl group having 1 to 4 carbon atoms, an alkoxyl group having 1 to 4 carbon atoms, or a phenyl group. In addition, Py represents a pyridyl group.

The halogenated triazole derivative (TAZ-2) is coupled with a compound (F1) obtained by substitution of boronic acid of pyridine or a compound of pyridine with organoboron by Suzuki-Miyaura Coupling using a palladium catalyst to obtain the triazole derivative (G1) having pyridine. Note that $X^2$ is preferably a bromo group or an iodine group.

As examples of a palladium catalyst which is used for Suzuki-Miyaura Coupling, palladium(II) acetate, tetrakis (triphenylphosphine)palladium(0), and the like can be given. In addition, as examples of a ligand of the palladium catalyst, tri(ortho-tolyl)phosphine, triphenylphosphine, tricyclohexylphosphine, and the like can be given. In addition, as examples of a base, organic bases such as sodium tert-butoxide and inorganic bases such as potassium carbonate and sodium carbonate can be given. Note that the palladium catalyst, the ligand thereof, and a base are not limited to those listed as examples.

Further, as a reaction solvent, the following can be given as examples: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; and a mixed solvent of ether such as ethylene glycol dimethyl ether and water. Although not limited to those examples, the mixed solvent of toluene and water, the mixed solvent of toluene, ethanol, and water, or the mixed solvent of ether and water is more preferable.

The triazole derivative of an embodiment of the present invention can be synthesized by the method described above as an example, or the like. Hereinafter, specific examples of the triazole derivatives of embodiments of the present invention are listed (the following structural formulae (1) to (46)). However, the embodiment of the present invention is not limited thereto.

[Chemical Formula 9]

(1)

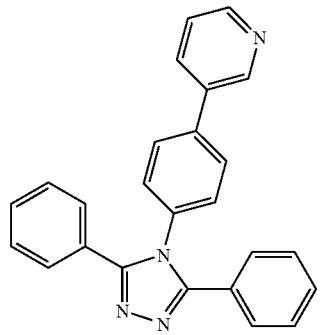

(2)

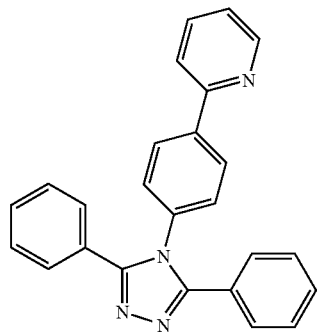

(3)

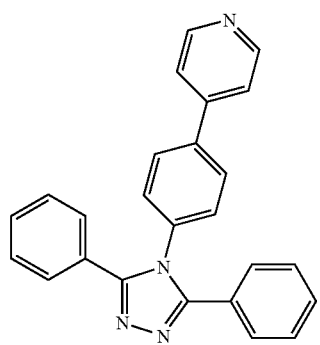

(4)

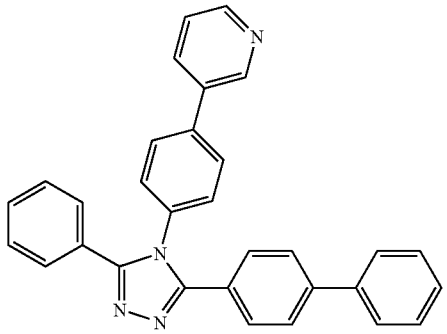

(5)

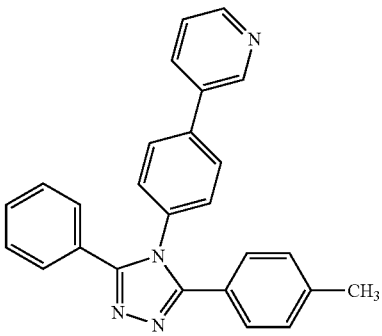

(6)

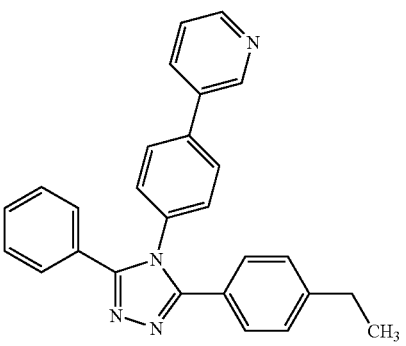

(7)

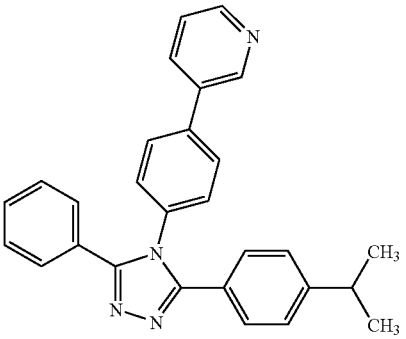

[Chemical Formula 10]
(8)
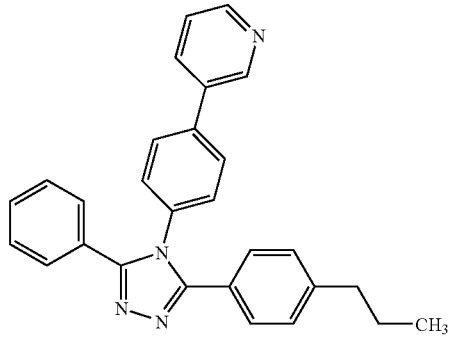
(9)
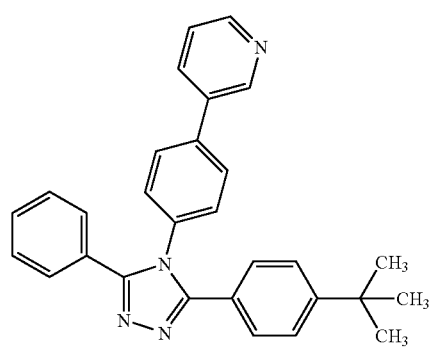
(10)
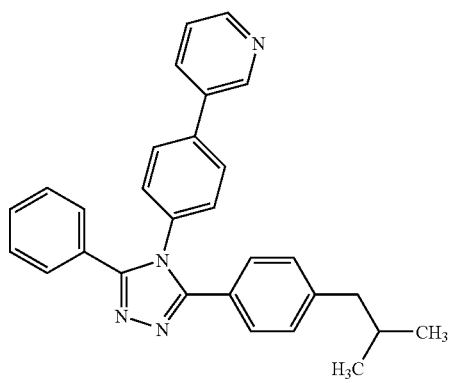
(11)
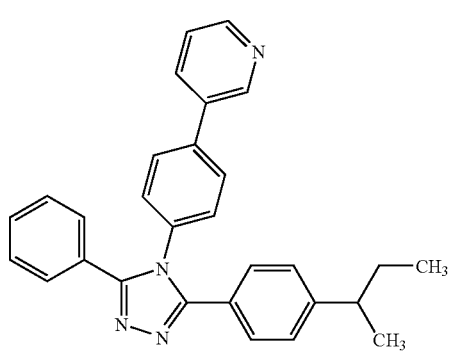
(12)
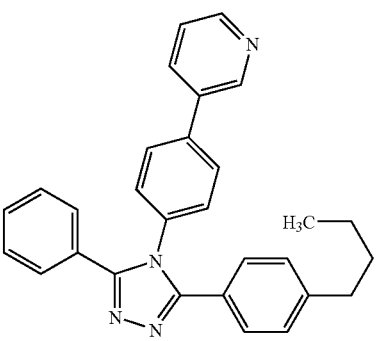
(13)
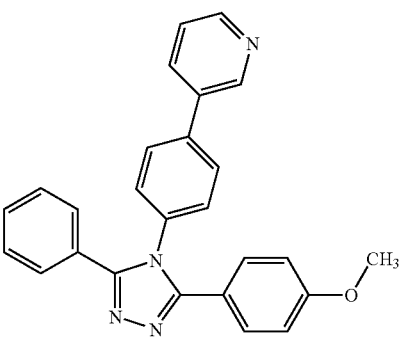
[Chemical Formula 11]
(14)
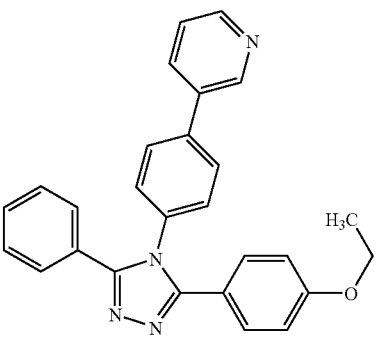
(15)
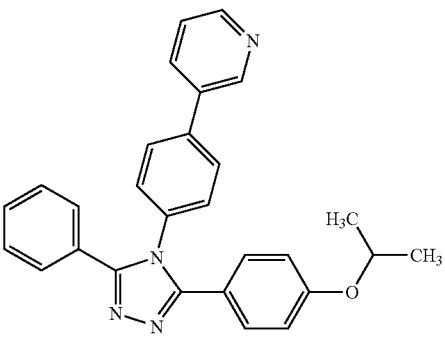

(16)
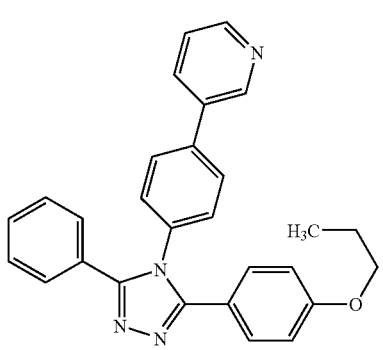
(17)
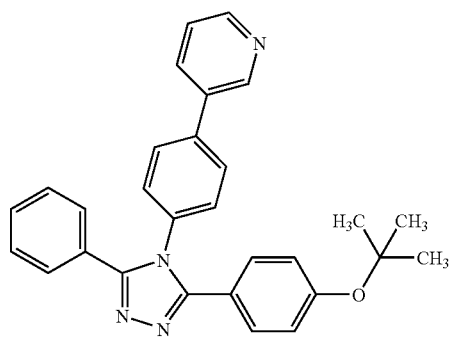
(18)
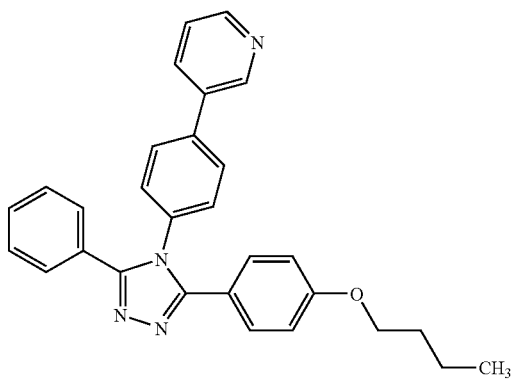
(19)
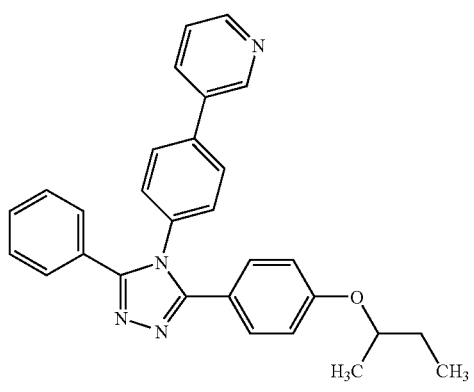
[Chemical Formula 12]
(20)
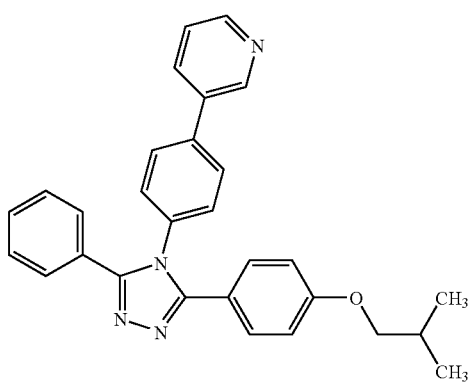
(21)
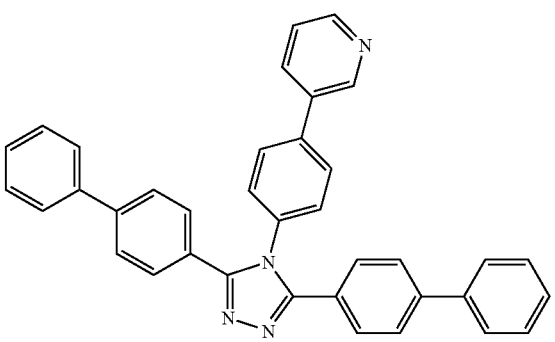
(22)
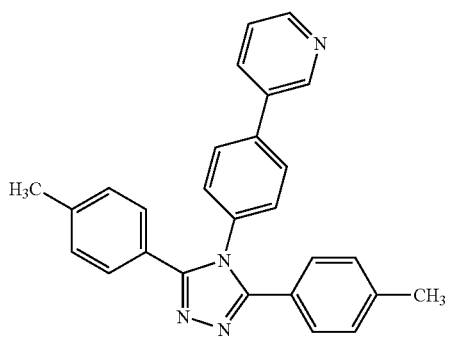
(23)
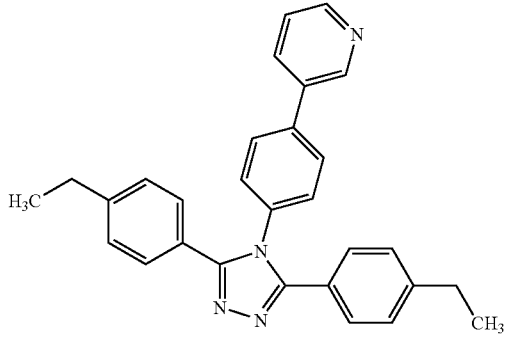

-continued
(24)
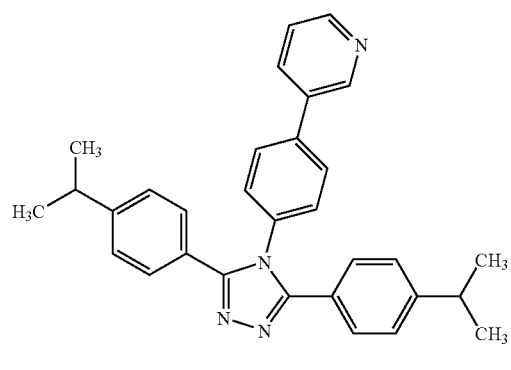
(25)
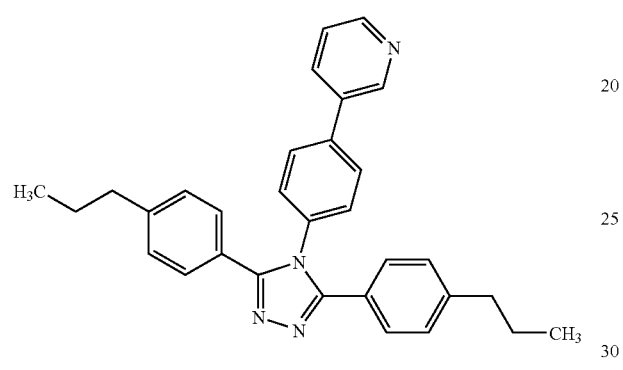
[Chemical Formula 13]
(26)
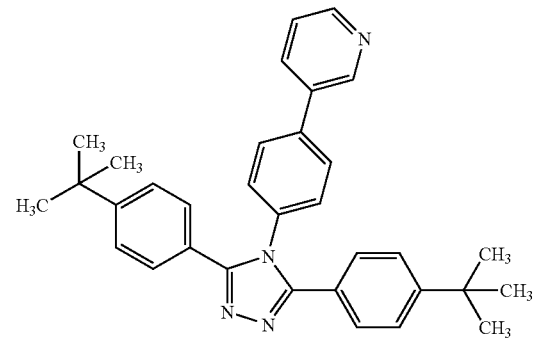
(27)
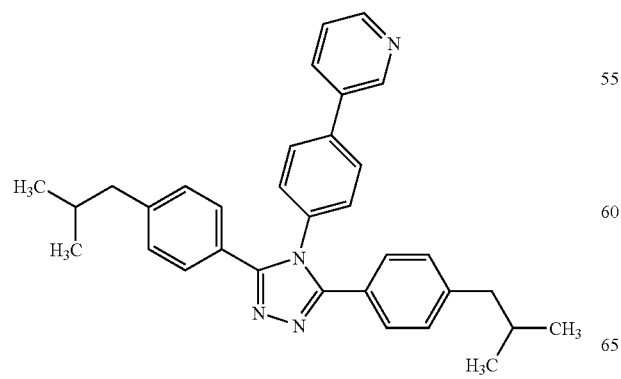
-continued
(28)
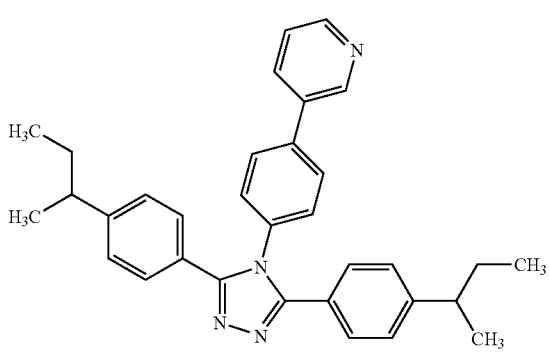
(29)
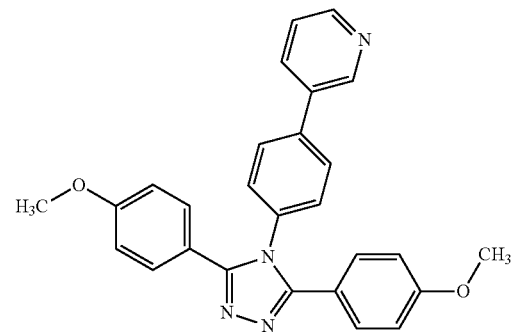
(30)
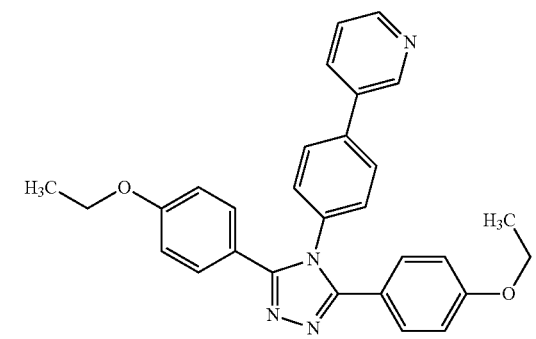
(31)

-continued

[Chemical Formula 14]

(32)
(33)
(34)
(35)
(36)
(37)

[Chemical Formula 15]

(38)
(39)

-continued

(40)
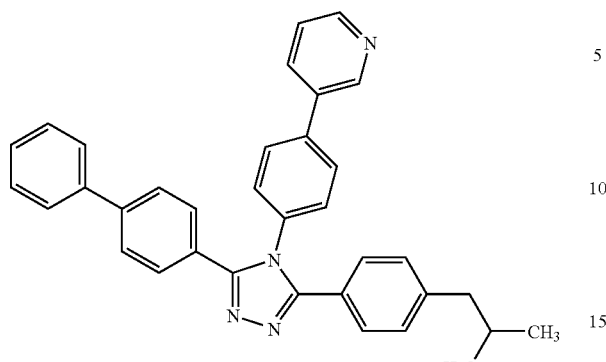

(41)
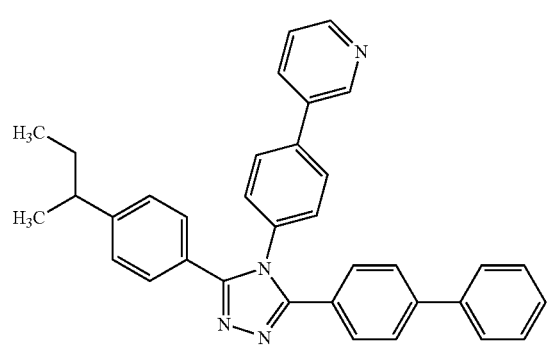

(42)
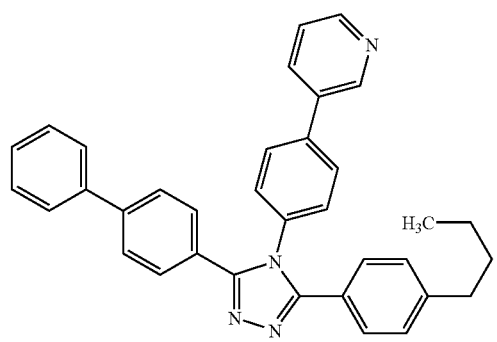

[Chemical Formula 16]

(43)
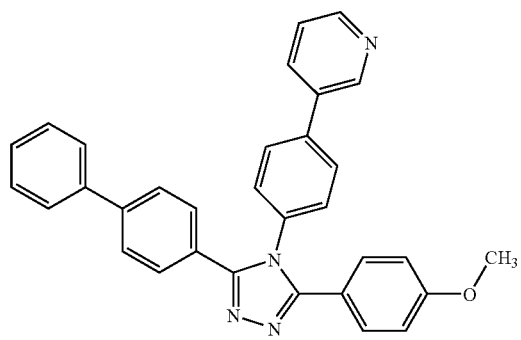

-continued

(44)
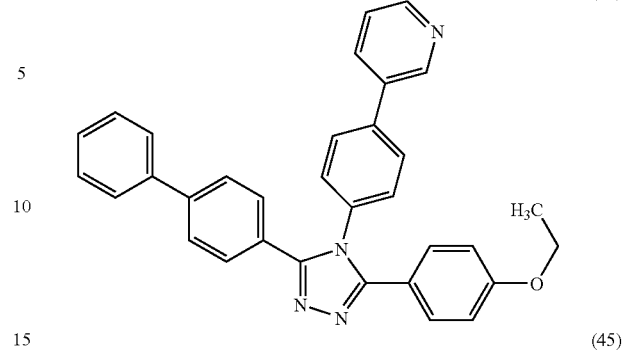

(45)
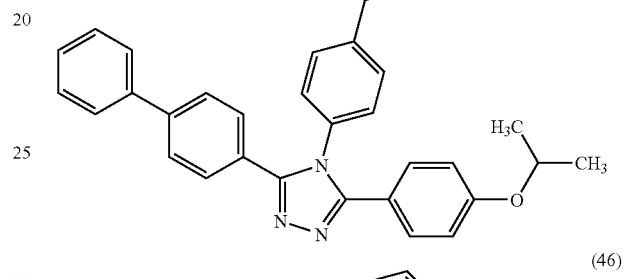

(46)
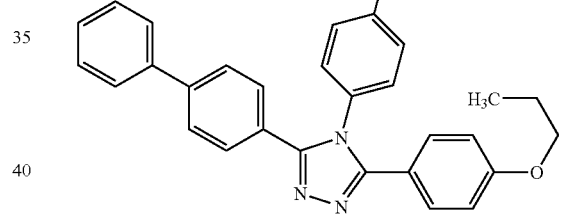

The above triazole derivatives of embodiments of the present invention have a large energy gap and an electron-transporting property, and therefore can be used as a host material which disperses a light-emitting substance or as an electron-transporting material.

Embodiment 2

In Embodiment 2, a mode of a light-emitting element in which the triazole derivative of an embodiment of the present invention is used as a host material of a phosphorescent compound will be described with reference to FIG. 1.

FIG. 1 illustrates a light-emitting element including a light-emitting layer 113 between a first electrode 101 and a second electrode 102. The light-emitting layer 113 contains the triazole derivative of an embodiment of the present invention which is described in Embodiment 1 and a light-emitting substance.

When voltage is applied to such a light-emitting element, holes injected from the first electrode 101 side and electrons injected from the second electrode 102 side are recombined in the light-emitting layer 113, whereby the light-emitting substance, for example, a phosphorescent compound is excited. Light is emitted when the phosphorescent compound in an excited state returns to a ground state. As described above, the triazole derivative of an embodiment of the present invention functions as a host material in the light-emitting layer of the light-emitting element. Note that the first electrode 101 and the second electrode 102 function as an anode and a cathode, respectively, in the light-emitting element of Embodiment 2.

The light-emitting layer 113 contains the triazole derivative of an embodiment of the present invention. The light-emitting layer 113 preferably has a structure in which a light-emitting substance is dispersed using the triazole derivative of an embodiment of the present invention as a host material. However, the triazole derivative of an embodiment of the present invention may be used by itself.

The triazole derivative of an embodiment of the present invention has high excitation energy and can be used as a host material of a blue light-emitting substance. In the case where the excitation energy of a host material is not sufficiently larger than that of a light-emitting substance, the energy of excitons move to the host material, which causes decrease in emission efficiency of the light-emitting element.

The light-emitting substance may be either a fluorescent compound or a phosphorescent compound. In terms of emission efficiency, a phosphorescent compound is preferably dispersed as a guest in the light-emitting layer. Further, the triazole derivative of an embodiment of the present invention in which a phosphorescent compound is dispersed is used, whereby a quenching phenomenon, that is, a phenomenon in which light emission is quenched due to concentration can be prevented.

In the case where a phosphorescent compound is used as a light-emitting substance, the triplet excitation energy of a host material of the phosphorescent compound needs to be higher than that of the phosphorescent compound. Note that the singlet excitation energy means a difference in energy between the ground state and the single excited state, and the triplet excitation energy means a difference in energy between the ground state and the triplet excited state.

Since the triazole derivative of an embodiment of the present invention has high triplet excitation energy, a light-emitting substance which is used for the light-emitting layer 113 is selected from a wide range of substances. For example, as the light-emitting layer 113, a light-emitting layer is used in which a phosphorescent compound is dispersed which exhibits light emission of a short wavelength, the emission peak wavelength of which is greater than or equal to 400 nm and less than or equal to 500 nm (blue and blue-tinged light emission) using the triazole derivative of an embodiment of the present invention as a host material, whereby a blue light-emitting element having high emission efficiency can be realized.

Organometallic complexes described below can be given as examples of the phosphorescent compound which can be used together with the triazole derivative of an embodiment of the present invention for the light-emitting layer 113.

As a light-emitting substance which exhibits blue and blue-tinged light emission, the following can be given: bis[2-(4′,6′-difluorophenyl)pyridinato-N,$C^{2′}$]iridium(III)tetrakis(1-pyrazolyl)borate (FIr6), bis[2-(4′,6′-difluorophenyl)pyridinato-N,$C^{2′}$]iridium(III)picolinate (FIrpic), bis{2-[3′,5′-bis(trifluoromethyl)phenyl]pyridinato-N,$C^{2′}$}iridium(III) picolinate (Ir($CF_3$ppy)$_2$(pic)), bis[2-(4′,6′-difluorophenyl)pyridinato-N,$C^{2′}$]iridium(III)acetylacetonate (FIracac), and the like.

As a light-emitting substance which exhibits green and green-tinged light emission, the following can be given: tris(2-phenylpyridinato-N,$C^{2′}$)iridium(III) (Ir(ppy)$_3$), bis[2-phenylpyridinato-N,$C^{2′}$]iridium(III)acetylacetonate (Ir(ppy)$_2$(acac)), bis(1,2-diphenyl-1H-benzimidazolato)iridium(III)acetylacetonate (Ir(pbi)$_2$(acac)), bis(benzo[h]quinolinato)iridium(III)acetylacetonate (Ir(bzq)$_2$(acac)), and the like.

As a light-emitting substance which exhibits yellow and yellow-tinged light emission, the following can be given: bis(2,4-diphenyl-1,3-oxazolato-N,$C^{2′}$)iridium(III)acetylacetonate (Ir(dpo)$_2$(acac)), bis{2-[4′-(perfluorophenylphenyl)pyridinato-N,$C^{2′}$]iridium(III)acetylacetonate (Ir(p-PF-ph)$_2$(acac)), bis(2-phenylbenzothiazolato-N,$C^{2′}$)iridium(III)acetylacetonate (Ir(bt)$_2$(acac)), and the like.

As a light-emitting substance which exhibits orange and orange-tinged light emission, the following can be given: tris(2-phenylquinolinato-N,$C^{2′}$)iridium(III) (Ir(pq)$_3$), bis(2-phenylquinolinato-N,$C^{2′}$)iridium(III)acetylacetonate (Ir(pq)$_2$(acac)), and the like.

As a light-emitting substance which exhibits red and red-tinged light emission, the following can be given: bis[2-(2′-benzo[4,5-α]thienyl)pyridinato-N,$C^{3′}$)iridium(III)acetylacetonate (Ir(btp)$_2$(acac)), bis(1-phenylisoquinolinato-N,$C^{2′}$)iridium(III)acetylacetonate (Ir(piq)$_2$(acac)), (acetylacetonato)bis[2,3-bis(4-fluorophenyl)quinoxalinato]iridium(III) (Ir(Fdpq)$_2$(acac)), (2,3,7,8,12,13,17,18-octaethyl-21H,23H-porphyrinato)platinum(II) (PtOEP), and the like.

In addition, a rare earth metal complex such as tris(acetylacetonato)(monophenanthroline)terbium(III) (Tb(acac)$_3$(Phen)), tris(1,3-diphenyl-1,3-propanedionato)(monophenanthroline)europium(III) (Eu(DBM)$_3$(Phen)), or tris[1-(2-thenyl)-3,3,3-trifluoroacetonato](monophenanthroline)europium(III) (Eu(TTA)$_3$(Phen)) performs light emission (electron transition between different multiplicities) from a rare earth metal ion; therefore, such a rare earth metal complex can be used as a phosphorescent compound.

Further, the triazole derivative of an embodiment of the present invention also has high singlet excitation energy; therefore, a variety of types of fluorescent compounds can be used for the light-emitting layer 113. Compounds described below can be given as examples of a fluorescent compound which can be used together with the triazole derivative of an embodiment of the present invention for the light-emitting layer 113.

As a light-emitting substance which exhibits blue and blue-tinged light emission, the following can be given: 2,5,8,11-tetra(tert-butyl)perylene (TBP), 4,4′-bis(2,2-diphenylvinyl)biphenyl (DPVBi), 4,4′-bis[2-(9-ethylcarbazol-3-yl)vinyl]biphenyl (BCzVBi), bis(2-methyl-8-quinolinolato)(4-phenylphenolato)aluminum (BAlq), bis(2-methyl-8-quinolinolato)galliumchloride (Gamq$_2$Cl), N,N′-bis[4-(9H-carbazol-9-yl)phenyl]-N,N′-diphenylstylbene-4,4′-diamine (YGA2S), 4-(9H-carbazol-9-yl)-4′-(10-phenyl-9-anthryl)triphenylamine (YGAPA), and the like.

As a light-emitting substance which exhibits green and green-tinged light emission, the following can be given: N-(9,10-diphenyl-2-anthryl)-N,9-diphenyl-9H-carbazol-3-amine (2PCAPA), N-[9,10-bis(1,1′-biphenyl-2-yl)-2-anthryl]-N,9-diphenyl-9H-carbazol-3-amine (2PCABPhA), N-(9,10-diphenyl-2-anthryl)-N,N′,N′-triphenyl-1,4-phenylenediamine (2DPAPA), N-[9,10-bis(1,1′-biphenyl-2-yl)-2-anthryl]-N,N′,N′-triphenyl-1,4-phenylenediamine (2DPABPhA), N-[9,10-bis(1,1′-biphenyl-2-yl)]-N-[4-(9H-carbazol-9-yl)phenyl]-N-phenylanthracen-2-amine (2YGABPhA); N,N,9-triphenylanthracen-9-amine (DPhAPhA), and the like.

As a light-emitting substance which exhibits yellow and yellow-tinged light emission, 5,12-bis(1,1′-biphenyl-4-yl)-6,11-diphenyltetracene (BPT), and the like can be given.

As a light-emitting substance which exhibits red and red-tinged light emission, the following can be given: N,N,N',N'-tetrakis(4-methylphenyl)tetracene-5,11-diamine (p-mPhTD), 7,13-diphenyl-N,N,N',N'-tetrakis(4-methylphenyl)acenaphtho[1,2-α]fluoranthene-3,10-diamine (p-mPhAFD), and the like.

As a host material which disperses the light-emitting substance, only the triazole derivative of an embodiment of the present invention may be used, or a mixture of the triazole derivative of an embodiment of the present invention and another material may be used. For example, a material in which the triazole derivative of an embodiment of the present invention and an organic compound having a hole-transporting property are mixed can be used as a host material.

Using, as a host, a material in which an organic compound having a hole-transporting property and an organic compound having an electron-transporting property are mixed is effective especially as a means of obtaining optimal carrier balance. In addition, a light-emitting region is expanded, whereby increase in emission efficiency of the light-emitting element and reliability thereof can be expected.

As an organic compound having a hole-transporting property which can be used as a host material by being mixed together with the triazole derivative of an embodiment of the present invention, the following can be used: an aromatic amine compound such as 4,4'-bis[N-(1-naphtyl)-N-phenylamino]biphenyl (NPB), 4,4'-bis[N-(9-phenanthryl)-N-phenylamino]biphenyl (PPB), 4,4'-bis[N-(3-methylphenyl)-N-phenylamino]biphenyl (TPD), 4,4'-bis[N-(9,9-dimethylfluoren-2-yl)-N-phenylamino]biphenyl (DFLDPBi), 4,4',4"-tris(N,N-diphenylamino)triphenylamine (TDATA), 4,4',4"-tris[N-(3-methylphenyl)-N-phenylamino]triphenylamine (m-MTDATA), 4,4',4"-tri(N-carbazolyl)triphenylamine (TCTA), 1,1-bis[4-(diphenylamino)phenyl]cyclohexane (TPAC), 9,9-bis[4-(diphenylamino)phenyl]fluorene (TPAF), 4-(9H-carbazolyl)-4'-(5-phenyl-1,3,4-oxadiazol-2-yl)triphenylamine (YGAO11), or N-[4-(9-carbazolyl)phenyl]-N-phenyl-9,9-dimethylfluoren-2-amine (YGAF); or a carbazole derivative such as 4,4'-di(N-carbazolyl)biphenyl (CBP), 1,3-bis(N-carbazolyl)benzene (mCP), or 1,3,5-tris(N-carbazolyl)benzene (TCzB).

The light-emitting layer 113 can be formed by, for example, a sputtering method, an evaporation method, or the like. By introduction of a substituent with a high volume, the cohesion of the triazole derivative of an embodiment of the present invention to which an alkyl group or an alkoxy group is introduced is suppressed and the sublimation property thereof is increased.

Application liquid in which the triazole derivative of an embodiment of the present invention and a light-emitting substance are dissolved or dispersed in an appropriate solvent is applied by a wet process such as an ink-jet method or a spin coating method, whereby the light-emitting layer 113 can be formed. The triazole derivative to which an alkyl group or an alkoxy group is introduced has high affinity with a solvent, and therefore can be used in combination with a variety of types of solvents.

The triazole derivative can be dissolved in a solvent having an aromatic ring (e.g., a benzene ring), such as toluene or methoxybenzene (anisole). Further, in addition to an organic solvent which does not have an aromatic ring, such as dimethylsulfoxide (DMSO), dimethylformamide (DMF), or chloroform; ether such as diethyl ether, dioxane, or tetrahydrofuran (THF); and alcohol such as methanol, ethanol, isopropanol, butanol, 2-methoxyethanol, or 2-ethoxyethanol, acetonitrile or a mixed solvent of the above can be used. However, the present invention is not limited thereto.

In the case where organic thin films are stacked by a wet process, application liquid needs to be formed by selection of a solvent which dissolves a material to be deposited but does not dissolve a layer which serves as a base. In addition, a volatile organic solvent, the boiling point of which is greater than or equal to 50° C. and less than or equal to 200° C., is preferably used so that the solvent does not remain in the film.

In the case where organic thin films are stacked by a wet process, a solution in which a light-emitting substance and the triazole derivative of an embodiment of the present invention are mixed may be applied, and furthermore the above organic compound having a hole-transporting property, a high molecular compound having a hole-transporting property, or a high molecular compound having an electron-transporting property may be added to the mixed solution.

Further, a binder may be contained in the solution in order to improve the property of a formed film. As the binder, a high molecular compound which is electrically inactive is preferably used. Specifically, polymethylmethacrylate (PMMA), polyimide, or the like can be used.

As a high molecular compound having a hole-transporting property, the following can be used: poly(N-vinylcarbazole) (PVK), poly(4-vinyltriphenylamine) (PVTPA), poly[N-(4-{N'-4-(4-diphenylamino)phenyl]phenyl-N'-phenylamino}phenyl)methacrylamide] (PTPDMA), poly[N,N'-bis(4-butylphenyl)-N,N'-bis(phenyl)benzidine (Poly-TPD), or the like.

In FIG. 1, a substrate 100 is used as a supporting body of the light-emitting element. As the substrate 100, for example, a glass substrate, a plastic substrate, or the like may be used. Note that substrates other than those substrates can be used as long as they can function as a supporting body of the light-emitting element.

Although there is no particular limitation on the first electrode 101, it is preferably formed using a substance having a high work function in the case of functioning as an anode as in this embodiment. Specifically, in addition to indium tin oxide (ITO), indium tin oxide containing silicon oxide (ITSO), and indium oxide containing zinc oxide at 2 wt % to 20 wt % (IZO), gold (Au), platinum (Pt), nickel (Ni), tungsten (W), chromium (Cr), molybdenum (Mo), iron (Fe), cobalt (Co), copper (Cu), palladium (Pd), or the like can be used. The first electrode 101 can be formed by, for example, a sputtering method, an evaporation method, or the like.

Further, although there is also no particular limitation on the second electrode 102, it is preferably formed using a substance having a low work function in the case of functioning as a cathode as in this embodiment. Specifically, in addition to aluminum (Al) and indium (In), alkali metal such as lithium (Li) or cesium (Cs); alkaline earth metal such as magnesium (Mg) or calcium (Ca); a rare-earth metal such as erbium (Er) or ytterbium (Yb); or the like can be used. In addition, an alloy such as aluminum-lithium alloy (AlLi) or magnesium-silver alloy (MgAg) can also be used. The second electrode 102 can be formed by, for example, a sputtering method, an evaporation method, or the like.

In order to extract emitted light to the outside, it is necessary that one or both of the first electrode 101 and the second electrode 102 be an electrode formed using a conductive film which can transmit visible light, such as ITO, or an electrode with a thickness of several nanometers to several tens of nanometers so as to transmit visible light.

In addition, as illustrated in FIG. 1, a hole-transporting layer 112 may be provided between the first electrode 101 and the light-emitting layer 113. The hole-transporting layer here means a layer which has a function of transporting holes, which are injected from the first electrode 101, to the light-emitting layer 113. In such a manner, the hole-transporting layer 112 is provided to separate the first electrode 101 from the light-emitting layer 113, whereby quenching of light emission due to metal can be prevented. However, the hole-transporting layer 112 is not necessarily provided.

Although there is no particular limitation on a substance forming the hole-transporting layer 112, the following can be typically used: an aromatic amine compound such as 4,4'-bis[N-(1-naphthyl)-N-phenylamino]biphenyl (NPB), 4,4'-bis[N-(3-methylphenyl)-N-phenylamino]biphenyl (TPD), 4,4'-bis[N-(9,9-dimethylfluoren-2-yl)-N-phenylamino]biphenyl (DFLDPBi), 4,4',4''-tris(N,N-diphenylamino)triphenylamine (TDATA), or 4,4',4''-tris[N-(3-methylphenyl)-N-phenylamino]triphenylamine (m-MTDATA). Furthermore, a high molecular compound such as poly(4-vinyl triphenylamine) (PVTPA) can also be used.

Note that the hole-transporting layer 112 may have a multilayer structure in which two or more layers are stacked. In addition, the hole-transporting layer 112 may also be formed by mixing two or more types of substances.

Further, as illustrated in FIG. 1, an electron-transporting layer 114 may be provided between the second electrode 102 and the light-emitting layer 113. The electron-transporting layer here means a layer which has a function of transporting electrons, which are injected from the second electrode 102, to the light-emitting layer 113. In such a manner, the electron-transporting layer 114 is provided to separate the second electrode 102 from the light-emitting layer 113, whereby quenching of light emission due to metal can be prevented. However, the electron-transporting layer 114 is not necessarily provided.

Although there is no particular limitation on a substance forming the electron-transporting layer 114, the following can be typically given: metal complexes such as tris(8-quinolinolato)aluminum ($Alq_3$), tris(4-methyl-8-quinolinolato) aluminum ($Almq_3$), bis(10-hydroxybenzo[h]quinolinato)beryllium ($BeBq_2$), bis(2-methyl-8-quinolinolato)(4-phenylphenolato)aluminum (BAlq), bis[2-(2-hydroxyphenyl)benzoxazolato]zinc (ZnBOX), and bis[2-(2-hydroxyphenyl)benzothiazolato]zinc ($Zn(BTZ)_2$). In addition, a heteroaromatic compound such as 2-(4-biphenylyl)-5-(4-tert-butylphenyl)-1,3,4-oxadiazole (PBD), 1,3-bis[5-(p-tert-butylphenyl)-1,3,4-oxadiazol-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), or 4,4'-bis(5-methylbenzoxazol-2-yl)stilbene (BzOs) can also be used. Furthermore, a high molecular compound such as poly(2,5-pyridine-diyl) (PPy) can also be used. Note that the electron-transporting layer 114 may have a multilayer structure in which two or more layers are stacked. In addition, the hole-transporting layer 112 may also be formed by mixing two or more types of substances.

Furthermore, as illustrated in FIG. 1, a hole-injecting layer 111 may be provided between the first electrode 101 and the hole-transporting layer 112. The hole-injecting layer here means a layer which has a function of assisting injection of holes from the electrode functioning as an anode into the hole-transporting layer 112. Note that the hole-injecting layer 111 is not necessarily provided.

Although there is no particular limitation on a substance forming the hole-injecting layer 111, the following can be used: metal oxide such as vanadium oxide, niobium oxide, tantalum oxide, chromium oxide, molybdenum oxide, tungsten oxide, manganese oxide, rhenium oxide, and ruthenium oxide. In addition, a phthalocyanine compound such as phthalocyanine ($H_2Pc$), copper phthalocyanine (CuPc), or the like can also be used. Moreover, any of the materials given above which are used to form the hole-transporting layer 112 can also be used. Furthermore, a high molecular compound such as a mixture of poly(ethylenedioxythiophene) and poly (styrene sulfonate) (PEDOT/PSS) can also be used.

Alternatively, a composite material in which an organic compound and an electron acceptor are mixed may be used for the hole-injecting layer 111. Such a composite material has excellent hole-injecting and hole-transporting properties because holes are generated in the organic compound by the electron acceptor. In that case, the organic compound is preferably a material which is excellent in transporting the generated holes: specifically, any of the substances given above which are used to form the hole-transporting layer 112 (such as aromatic amine compounds) can be used.

As the electron acceptor, any substance which shows an electron-accepting property with respect to the organic compound may be used. Specifically, transition metal oxide is preferable and examples thereof include vanadium oxide, niobium oxide, tantalum oxide, chromium oxide, molybdenum oxide, tungsten oxide, manganese oxide, rhenium oxide, ruthenium oxide, and the like. Alternatively, an organic compound such as 7,7,8,8-tetracyano-2,3,5,6-tetrafluoroquinodimethane ($F_4$-TCNQ) can also be used. Note that the hole-injecting layer 111 may have a multilayer structure in which two or more layers are stacked. In addition, the hole-transporting layer 112 may also be formed by mixing two or more types of substances.

Furthermore, as illustrated in FIG. 1, an electron-injecting layer 115 may be provided between the second electrode 102 and the electron-transporting layer 114.

The electron-injecting layer here means a layer which has a function of assisting injection of electrons from the electrode functioning as a cathode into the electron-transporting layer 114. However, the electron-injecting layer 115 is not necessarily provided.

Although there is no particular limitation on a substance forming the electron-injecting layer 115, an alkali metal compound or an alkaline earth metal compound such as lithium fluoride (LiF), cesium fluoride (CsF), calcium fluoride ($CaF_2$), or lithium oxide can be used. In addition, a rare earth metal compound such as erbium fluoride ($ErF_3$) can also be used. Any of the substances forming the electron-transporting layer 114 which are given above can also be used.

A composite material in which an organic compound and an electron donor are mixed may be used for the electron-injecting layer 115. Such a composite material has excellent electron-injecting and electron-transporting properties because electrons are generated in the organic compound by the electron donor. In that case, the organic compound is preferably a material which is excellent in transporting the generated electrons: specifically, any of the substances given above which are used to form the electron-transporting layer 114 (such as metal complexes and heteroaromatic compounds) can be used. As the electron donor, any substance which shows an electron-donating property with respect to the organic compound may be used. Specifically, alkali metal, alkaline earth metal, and rare earth metal are preferable, and lithium, cesium, magnesium, calcium, erbium, ytterbium, and the like are given. Further, alkali metal oxide or alkaline earth metal oxide such as lithium oxide, calcium oxide, barium oxide, and the like can be given. Lewis base such as magnesium oxide can also be used. In addition, an organic compound such as tetrathiafulvalene (TTF) can also be used.

In the above light-emitting element of an embodiment of the present invention, each of the hole-injecting layer 111, the hole-transporting layer 112, the light-emitting layer 113, the electron-transporting layer 114, and the electron-injecting layer 115 may be formed by any of an evaporation method, an ink-jet method, and a coating method. In addition, each of the first electrode 101 and the second electrode 102 may also be formed by any of wet processes such as a sputtering method, an evaporation method, an ink-jet method, and a coating method.

The triazole derivative of an embodiment of the present invention can be favorably used for the light-emitting layer because it has a large energy gap. In particular, the triazole derivative of an embodiment of the present invention can be used as a host material of a phosphorescent compound which exhibits blue and blue-tinged light emission of a short wavelength, the emission peak wavelength of which is greater than or equal to 400 nm and less than or equal to 500 nm. As a result, a blue light-emitting element having excellent emission efficiency can be manufactured.

Note that Embodiment 2 can be combined with any of the other embodiments as appropriate.

Embodiment 3

In Embodiment 3, a light-emitting element having a structure different from that of the light-emitting element described in Embodiment 2 will be described.

The triazole derivative described in Embodiment 1 has an electron-transporting property, and therefore can be used for an electron-transporting layer. Especially in the case where the triazole derivative described in Embodiment 1 is used for an electron-transporting layer, driving voltage of a light-emitting element can be reduced.

Further, the triazole derivative described in Embodiment 1 has high triplet excitation energy and high singlet excitation energy; therefore, energy transfer from a light-emitting layer is less likely to occur in the case where the triazole derivative described in Embodiment 1 is used for a layer in contact with the light-emitting layer. Accordingly, high emission efficiency can be realized.

Further, the triazole derivative described in Embodiment 1 does not easily transport holes, and therefore can be used for a hole-blocking layer. Holes which fail to be recombined in the light-emitting layer can be prevented from running to the cathode side. Accordingly, not only emission efficiency but also reliability of the light-emitting element can be increased.

Note that Embodiment 3 can be combined with any of the other embodiments as appropriate.

Embodiment 4

The light-emitting element of an embodiment of the present invention may include a plurality of light-emitting layers. A plurality of light-emitting layers are provided and light is emitted from each of the light-emitting layers, whereby light emission in which a plurality of types of light are mixed can be obtained. Thus, for example, white light emission can be obtained. In Embodiment 4, a mode of a light-emitting element including a plurality of light-emitting layers will be described with reference to FIG. 2.

Figure 2:
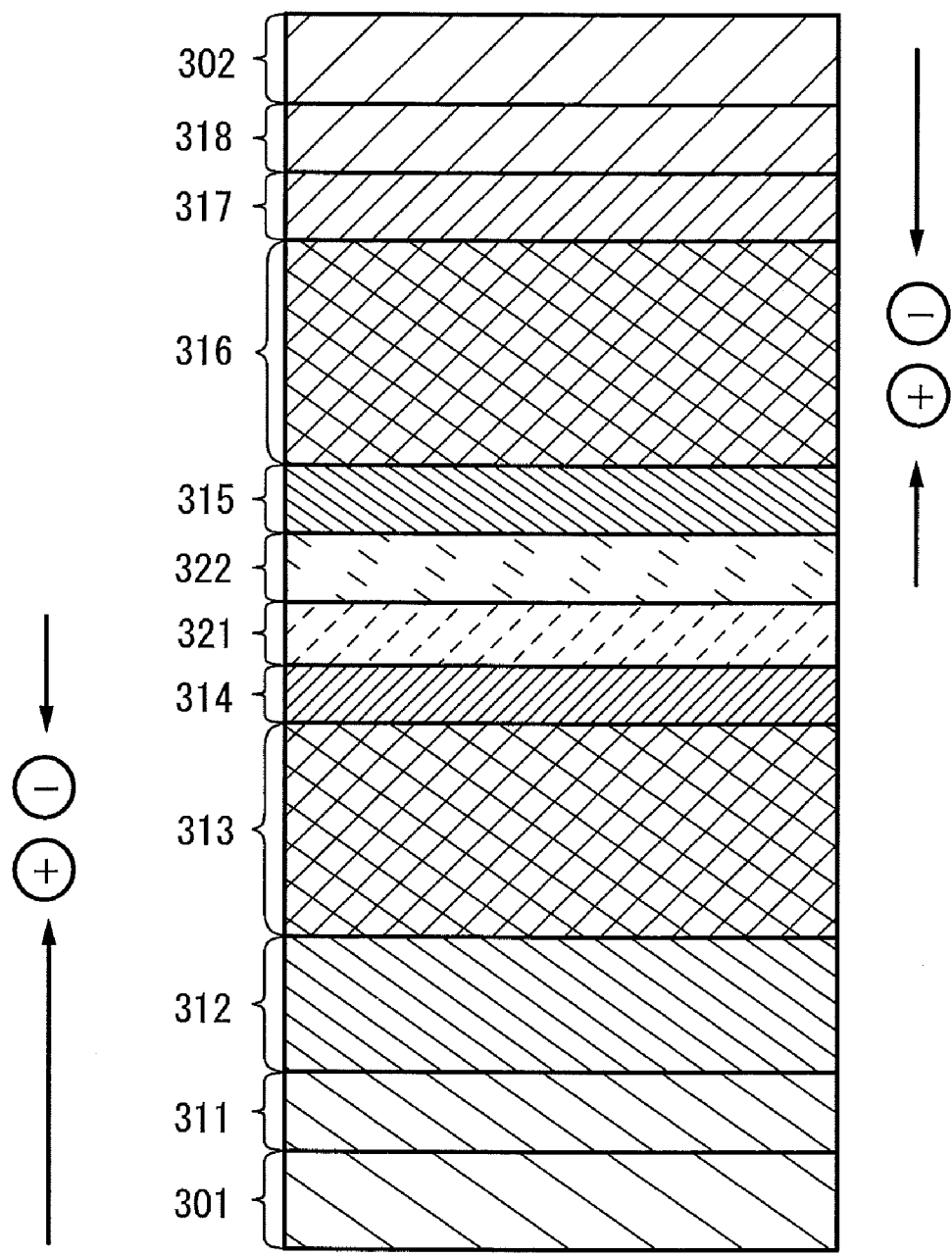
FIG. 2 illustrates a light-emitting element according to Embodiment.

In a light-emitting element illustrated in FIG. 2, a first light-emitting layer 313 and a second light-emitting layer 316 are provided between a first electrode 301 and a second electrode 302. In addition, an N layer 321 and a P layer 322 are provided as charge generating layers between the first light-emitting layer 313 and the second light-emitting layer 316.

The N layer 321 is a layer which generates electrons and the P layer 322 is a layer which generates holes. When voltage is applied so that the potential of the first electrode 301 becomes higher than that of the second electrode 302, holes injected from the first electrode 301 and electrons injected from the N layer 321 are recombined in the first light-emitting layer 313; accordingly, a first light-emitting substance contained in the first light-emitting layer 313 emits light. Furthermore, electrons injected from the second electrode 302 and holes injected from the P layer 322 are recombined in the second light-emitting layer 316; accordingly, a second light-emitting substance contained in the second light-emitting layer 316 emits light.

The structures of the first light-emitting layer 313 and the second light-emitting layer 316 may be similar to that of the light-emitting layer 113 in Embodiment 2. For example, one of the light-emitting layers may contain a fluorescent light-emitting substance and the other may contain a phosphorescent light-emitting substance. Alternatively, both of the layers may contain either a fluorescent light-emitting substance or a phosphorescent light-emitting substance.

Here, for the first light-emitting layer 313, a substance is used in which a phosphorescent compound with which light emission having emission spectrum peak at 450 nm to 510 nm (that is, light emission ranging from blue to blue green) can be obtained or a fluorescent compound is dispersed in the triazole derivative of an embodiment of the present invention. The triazole derivative of an embodiment of the present invention has a large energy gap, and therefore can be used as a host material of a blue light-emitting substance.

On the other hand, for the second light-emitting layer 316, a substance is used in which a phosphorescent compound with which red light emission can be obtained or a fluorescent compound is dispersed in the triazole derivative of an embodiment of the present invention. The triazole derivative of an embodiment of the present invention has a large energy gap, and therefore can be used as a host material of a variety of types of light-emitting substances which emit light ranging from blue to red.

For example, bis[2-(4',6'-difluorophenyl)pyridinato-N, $C^{2'}$]iridium(III)picolinate (FIrpic) which exhibits blue light emission is used as a light-emitting substance of the first light-emitting layer 313 and bis[2,3-bis(4-fluorophenyl)-5,6,7,8-tetrahydroquinoxalinato](picolinato)iridium(III) (Ir(FdpqtH)$_2$(pic)) is used as a light-emitting substance of the second light-emitting layer 316, whereby a white light-emitting element can be obtained.

Since the N layer 321 is a layer which generates electrons, it may be formed using the composite material in which the organic compound and the electron donor described above in Embodiment 2 are mixed. Such a structure enables electrons to be injected to the first light-emitting 313 side.

Since the P layer 322 is a layer which generates holes, it may be formed using the composite material in which the organic compound and the electron acceptor described above in Embodiment 2 are mixed. Such a structure enables holes to be injected to the second light-emitting layer 316 side. Alternatively, for the P layer 322, metal oxide having an excellent hole-injecting property, such as molybdenum oxide, vanadium oxide, ITO, or ITSO, can be used.

Although the light-emitting element including two light-emitting layers is described in Embodiment 4, the number of light-emitting layers is not limited to two and may be three, for example. Light emission from each light-emitting layer may be mixed. As a result, for example, white light emission can be obtained.

The structure of the first electrode 301 may be similar to that of the first electrode 101 described above in Embodiment 2. In addition, the structure of the second electrode 302 may be similar to that of the second electrode 102 described above in Embodiment 2.

Further, in Embodiment 4, as illustrated in FIG. 2, the hole-injecting layer 311, the hole-transporting layers 312 and 315, the electron transporting layers 314 and 317, and the electron-injecting layer 318 are provided. The structures of the layers described above in Embodiments 2 and 3 may be applied to the structures of the above layers. However, those layers are not necessarily provided and may be provided depending on the element characteristics.

In the case where the triazole derivative of an embodiment of the present invention is used for the electron-transporting layer in contact with the light-emitting layer, an excellent electron-transporting property is obtained and driving voltage of the light-emitting element can be reduced. In addition, the triazole derivative of an embodiment of the present invention has a large energy gap; therefore, energy transfer from excitons of the light-emitting layer is difficult, and thus emission efficiency less likely to decrease.

Further, in the case where the triazole derivative of an embodiment of the present invention is used for the light-emitting layer, the triazole derivative can be used as a host material of a phosphorescent compound which exhibits blue and blue-tinged light emission of a short wavelength, the emission peak wavelength of which is greater than or equal to 400 nm and less than or equal to 500 nm. As a result, like a stacked type light-emitting element of Embodiment 4, a white light-emitting element having excellent emission efficiency can be manufactured in which only a phosphorescent compound which is superior to a fluorescent compound in terms of emission efficiency is used as a light-emitting substance.

With use of the light-emitting element in which the triazole derivative of an embodiment of the present invention is used as described above, a low power consumption light-emitting device can be realized.

Arrangement of a plurality of light-emitting units, which are partitioned by a charge generation layer between a pair of electrodes as in the light-emitting element of Embodiment 4, makes it possible to realize a long-life element in a high luminance region, with the current density kept low. In addition, in the case where the light-emitting element is applied to a lighting system, uniform light emission in a large area is possible because voltage drop due to resistance of an electrode material can be decreased.

Note that Embodiment 4 can be combined with any of the other embodiments as appropriate.

Embodiment 5

In Embodiment 5, a light-emitting device manufactured using the triazole derivative of an embodiment of the present invention will be described with reference to FIGS. 3A and 3B and FIGS. 4A and 4B. FIG. 3A is a top view of the light-emitting device and FIG. 3B is a cross-sectional view of FIG. 3A taken along the line A-A'. Reference numerals 401, 402 and 403, which are shown by dotted lines, denote a driver circuit portion (a source driver circuit), a pixel portion, and a driver circuit portion (a gate driver circuit), respectively. Reference numeral 404 denotes a sealing substrate, reference numeral 405 denotes a sealing material, and a portion enclosed by the sealing material 405 is a space 407.

A lead wiring 408 is a wiring for transmitting a signal to be inputted to the source driver circuit 401 and the gate driver circuit 403, and receives a video signal, a clock signal, a start signal, a reset signal, and the like from a flexible printed circuit (FPC) 409 which serves as an external input terminal. Although only the FPC is illustrated in FIGS. 3A and 3B, a printed wiring board (PWB) may be attached to the FPC. The light-emitting device in this specification includes, in its category, not only a light-emitting device itself but also a light-emitting device with an FPC or a PWB attached thereto.

Next, a cross-sectional structure will be described with reference to FIG. 3B. Although the driver circuit portions and the pixel portion having a plurality of pixels are formed over a substrate 410, the source driver circuit 401 which is a driver circuit portion and one of the plurality of pixels in the pixel portion 402 are illustrated here.

As the source driver circuit 401, a CMOS circuit which is obtained by combining an n-channel TFT 423 and a p-channel TFT 424 is formed. A TFT for forming the driver circuit may be formed using a known CMOS circuit, a PMOS circuit, or an NMOS circuit. Although a driver integration type in which a driver circuit is formed over a substrate is described in Embodiment 5, a driver circuit is not necessarily formed over a substrate and can be formed outside a substrate.

The pixel portion 402 is formed of a plurality of pixels each of which includes a switching TFT 411, a current control TFT 412, and a first electrode 413 electrically connected to a drain of the current control TFT 412. An insulator 414 is formed to cover an end portion of the first electrode 413. Here, the insulator 414 is formed using a positive photosensitive acrylic resin film.

The insulator 414 is formed so as to have a curved surface having curvature at an upper end portion or a lower end portion thereof in order to obtain favorable coverage. For example, when positive photosensitive acrylic is used as a material for the insulator 414, the insulator 414 preferably has a curved surface with a curvature radius (0.2 μM to 3 μm) only as the upper end. Either a negative type which becomes insoluble in an etchant by light or a positive type which becomes soluble in an etchant by light can be used as the insulator 414.

A layer 416 containing a light-emitting substance and a second electrode 417 are formed over the first electrode 413. It is desirable to use a material having a high work function as a material for forming the first electrode 413 which functions as the anode. For example, the first electrode 413 can be formed using a stacked layer of a titanium nitride film and a film containing aluminum as its main component; a three-layer structure of a titanium nitride film, a film containing aluminum as its main component, and another titanium nitride film; or the like, as well as a single-layer film such as an indium tin oxide (ITO) film, an indium tin oxide film containing silicon, an indium zinc oxide (IZO) film, a titanium nitride film, a chromium film, a tungsten film, a Zn film, or a Pt film. In the case of a stacked-layer structure, the first electrode 413 has low resistance as a wiring, which results in a favorable ohmic contact and can further function as an anode.

The layer 416 containing a light-emitting substance, which is interposed between the first electrode 413 and the second electrode 417, is formed in a manner similar to that in Embodiments 2 to 4, and the triazole derivative of an embodiment of the present invention described in Embodiment 1 is used for part of the layer 416. As a material which can be used by being combined with the triazole derivative of an embodiment of the present invention, a low molecular material, an oligomer, a dendrimer, or a high molecular material may be used. In addition, as a material used for the layer containing a light-emitting substance, a single layer or a stacked layer of an organic compound is generally used. However, the present invention also includes a structure in which an inorganic compound is used for part of a film formed of the organic compound.

The layer 416 containing a light-emitting substance is formed by a variety of methods such as an evaporation method using an evaporation mask, an ink-jet method, and a spin coating method.

As a material used for the second electrode 417 to be formed over the layer 416 containing a light-emitting substance, a material having a low work function (Al, Ag, Li, Ca, or an alloy or a compound of them, such as MgAg, MgIn, AlLi, LiF, $CaF_2$, calcium nitride, or calcium fluoride) is preferably used. In the case where light emitted from the layer 416 containing a light-emitting substance is transmitted through the second electrode 417 which functions as a cathode, a stacked layer of a metal thin film with reduced thickness and a transparent conductive film (formed using an indium tin oxide alloy (ITO), an indium oxide-zinc oxide alloy ($In_2O_3$—ZnO), zinc oxide (ZnO), or the like) is preferably used as the second electrode 417.

Attachment of the sealing substrate 404 to the substrate 410 with the sealing material 405 makes a structure in which a light-emitting element 418 is provided in the space 407 surrounded by the substrate 410, the sealing substrate 404, and the sealing material 405. Structures in which the space 407 is filled with an inert gas (such as nitrogen or argon) and the space 407 is filled with the sealing material 405 are included in the present invention.

It is preferable to use an epoxy-based resin for the sealing material 405. In addition, it is desirable that the material transmit as little moisture and oxygen as possible. As the sealing substrate 404, a plastic substrate made of fiberglass-reinforced plastics (FRP), polyvinyl fluoride (PVF), polyester, an acrylic resin, or the like can be used besides a glass substrate or a quartz substrate.

As described above, a light-emitting device which is manufactured using the triazole derivative of an embodiment of the present invention can be obtained.

Since the triazole derivative described in Embodiment 1 is used for the light-emitting device of an embodiment of the present invention, a light-emitting device having favorable characteristics can be obtained. Specifically, since a light-emitting element having high emission efficiency is included, a light-emitting device with low power consumption and capability of long-time driving can be obtained.

Figure 4A:
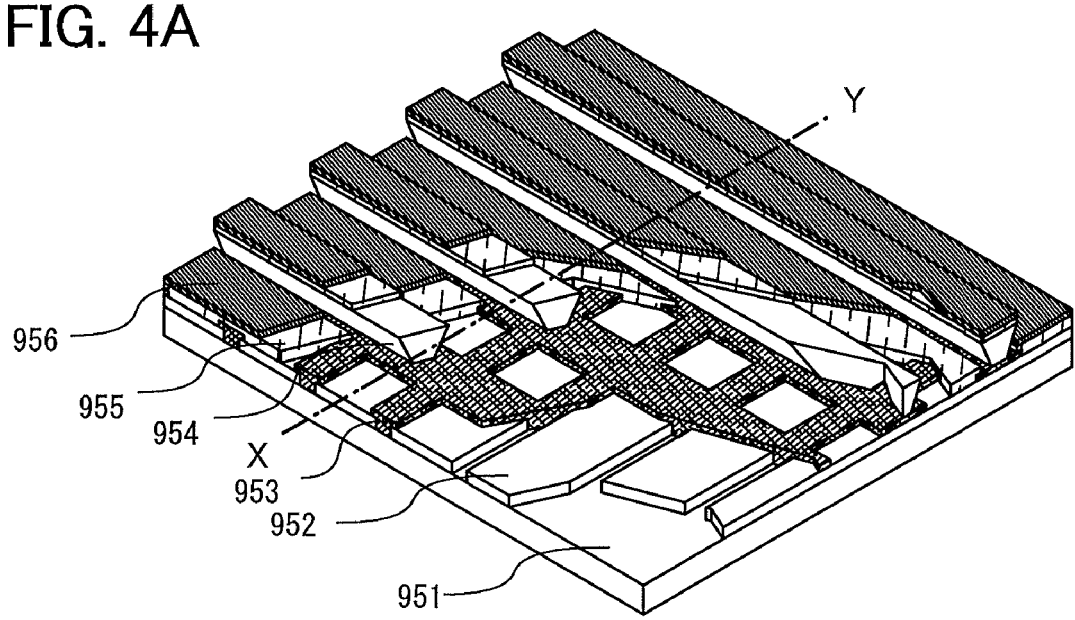
FIGS. 4A and 4B illustrate a light-emitting device according to Embodiment.
Figure 4B:
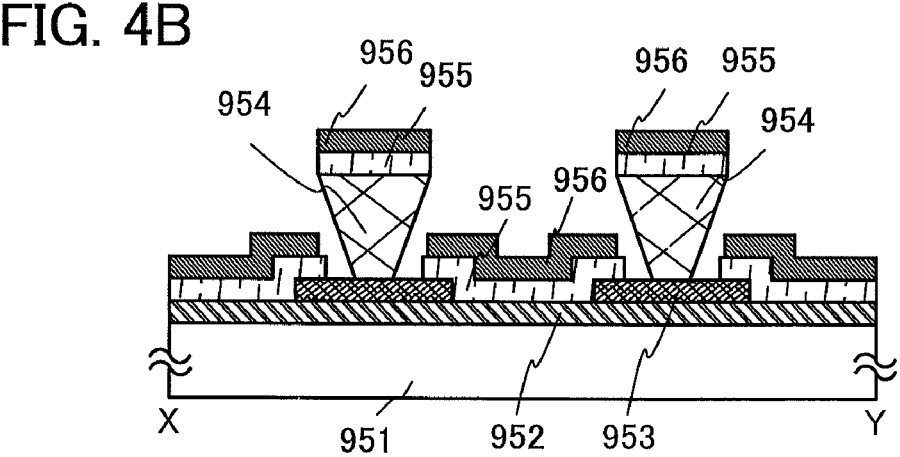

Although, as described above, description is made on an active matrix image display device which controls driving of a light-emitting element using transistors, the present invention may include a passive matrix image display device. FIGS. 4A and 4B illustrate a passive matrix image display device manufactured using an embodiment of the present invention. FIG. 4A is a perspective view illustrating the passive matrix image display device and FIG. 4B is a cross-sectional view of FIG. 4A taken along the line X-Y. In FIGS. 4A and 4B, an electrode 952 and an electrode 956 are provided over a substrate 951, and a layer 955 containing a light-emitting substance is provided between the electrode 952 and the electrode 956. The edge of the electrode 952 is covered with an insulating layer 953. A partition wall layer 954 is provided over the insulating layer 953.

The sidewalls of the partition wall layer 954 slope so that a distance between both sidewalls is gradually narrowed toward the surface of the substrate. That is, a cross section in the direction of a narrow side of the partition wall layer 954 has a trapezoidal shape, and a lower side (which faces a surface of the insulating layer 953 and is in contact with the insulating layer 953) is shorter than an upper side (which faces the surface of the insulating layer 953 and is not in contact with the insulating layer 953). The partition wall layer 954 is provided in this manner, whereby defects of the light-emitting element due to static electricity can be prevented.

The layer 955 containing a light-emitting substance which is interposed between the electrode 952 and the electrode 956 is formed in a manner similar to that in Embodiments 2 to 4, and the triazole derivative of an embodiment of the present invention which is described in Embodiment 1 is used for part of the layer 955.

Since the triazole derivative described in Embodiment 1 is used for the light-emitting device of an embodiment of the present invention, the light-emitting device can obtain favorable characteristics. Specifically, since the light-emitting device includes a light-emitting element having high emission efficiency, it has low power consumption and can be driven for a long time.

Embodiment 6

In Embodiment 6, electronic devices of an embodiment of the present invention each of which includes the light-emitting device described in Embodiment 5 as part thereof will be described. The electronic device of an embodiment of the present invention includes the triazole derivative described in Embodiment 1, and thus includes a display portion having high emission efficiency, low power consumption, and capability of long-time driving. In addition, the electronic device of an embodiment of the present invention includes a display portion having excellent color reproducibility.

As examples of the electronic devices each of which includes a light-emitting element manufactured using the triazole derivative of an embodiment of the present invention, the following are given: cameras such as video cameras or digital cameras, goggle type displays, navigation systems, audio reproducing devices (e.g., car audio components and audio components), computers, game machines, portable information terminals (e.g., mobile computers, cellular phones, portable game machines, and electronic books), and image reproducing devices provided with recording media (specifically, a device capable of reproducing recording media such as digital versatile discs (DVDs) and provided with a display device that can display the image). Specific examples of those electronic devices are illustrated in FIGS. 5A to 5D.

Figure 5A:
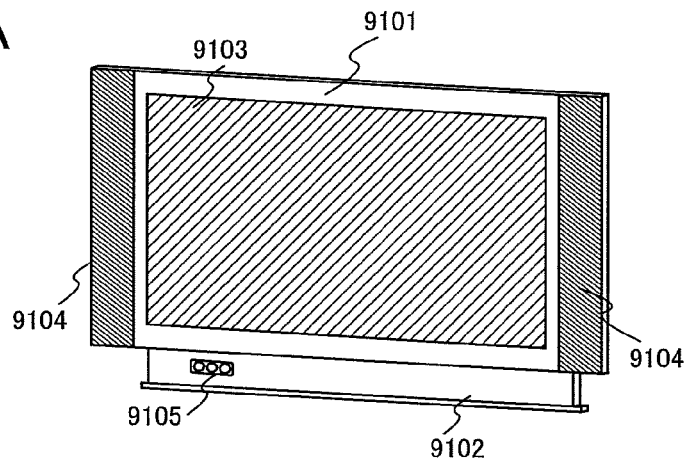
FIGS. 5A to 5D each illustrate an electronic device according to Embodiment.

FIG. 5A illustrates a television set according to an embodiment of the present invention. The television set includes a housing 9101, a supporting base 9102, a display portion 9103, a speaker portion 9104, a video input terminal 9105, and the like. In the display portion 9103 of this television set, light-emitting elements similar to those described in Embodiments 2 to 4 are arranged in a matrix. The light-emitting elements have such an advantage that the emission efficiency is high. The display portion 9103 which includes the light-emitting elements has similar features to achieve light emission with high luminance and reduction in power consumption. The television set according to an embodiment of the present invention achieves low power consumption and high image quality, and thus can be provided as a product which is suitable for any residential environment.

Figure 5B:
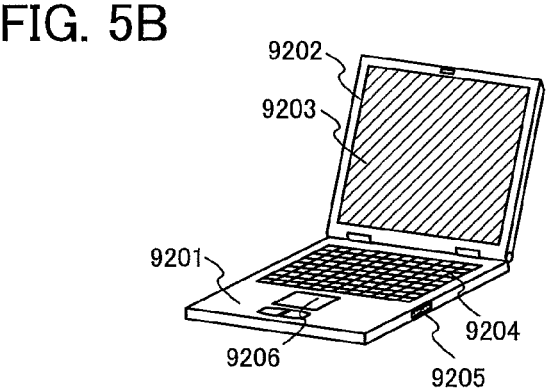

FIG. 5B illustrates a computer according to an embodiment of the present invention. The computer includes a main body 9201, a chassis 9202, a display portion 9203, a keyboard 9204, an external connection port 9205, a pointing device 9206, and the like. In the display portion 9203 of this computer, light-emitting elements similar to those described in Embodiments 2 to 4 are arranged in a matrix. The light-emitting elements have such an advantage that the luminous efficiency is high. The display portion 9203 which includes the light-emitting elements has similar features to achieve light emission with high luminance and reduction in power consumption. The computer according to an embodiment of the present invention achieves low power consumption and high image quality, and thus can be provided as a product which is suitable for any environment.

Figure 5C:
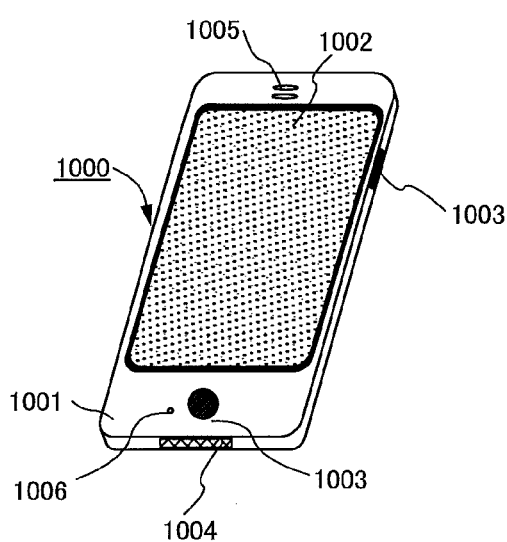

FIG. 5C illustrates a cellular phone according to embodiment of the present invention. Information can be inputted when a display portion 1002 is touched with a finger or the like. Users can make a call or text by touching the display portion 1002 with their fingers or the like. In the display portion 1002 of this cellular phone, light-emitting elements similar to those described in Embodiments 2 to 4 are arranged in a matrix. The light emitting elements have such an advantage that the emission efficiency is high. The display portion 1002 which includes the light-emitting elements has similar features to achieve light emission with high luminance and reduction in power consumption. The computer according to an embodiment of the present invention achieves low power consumption and high image quality, and thus can be provided as a product which is suitable for portable use.

Figure 5D:
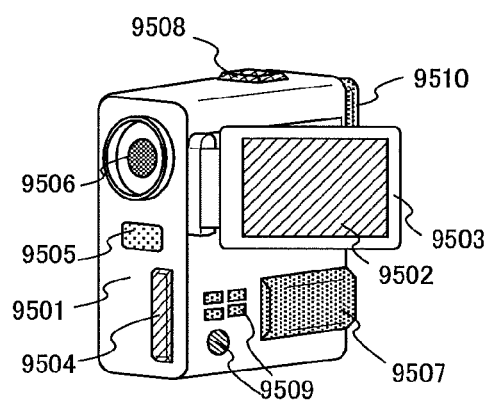

FIG. 5D illustrates a camera according to an embodiment of the present invention. The camera includes a main body 9501, a display portion 9502, a housing 9503, an external connection port 9504, a remote control receiving portion 9505, an image receiving portion 9506, a battery 9507, an audio input portion 9508, operation keys 9509, an eyepiece portion 9510, and the like. In the display portion 9502 of this computer, light-emitting elements similar to those described in Embodiments 2 to 4 are arranged in a matrix. The light-emitting elements have such an advantage that the luminous efficiency is high and long-time driving is possible. The display portion 9502 which includes the light-emitting elements has similar features to achieve light emission with high luminance and reduction in power consumption. The camera according to an embodiment of the present invention achieves low power consumption and high image quality, and thus can be provided as a product which is suitable for portable use.

As described above, the applicable range of the light-emitting device of an embodiment of the present invention is so wide that the light-emitting device can be applied to electronic devices in a variety of fields. Use of the triazole derivative of an embodiment of the present invention enables electronic devices each including a display portion having high emission efficiency, capability of long-time driving, and low power consumption to be provided.

Further, the light-emitting device of an embodiment of the present invention can also be used as a lighting system. One mode of using the light-emitting element of an embodiment of the present invention as a lighting system will be described with reference to FIG. 6.

Figure 6:
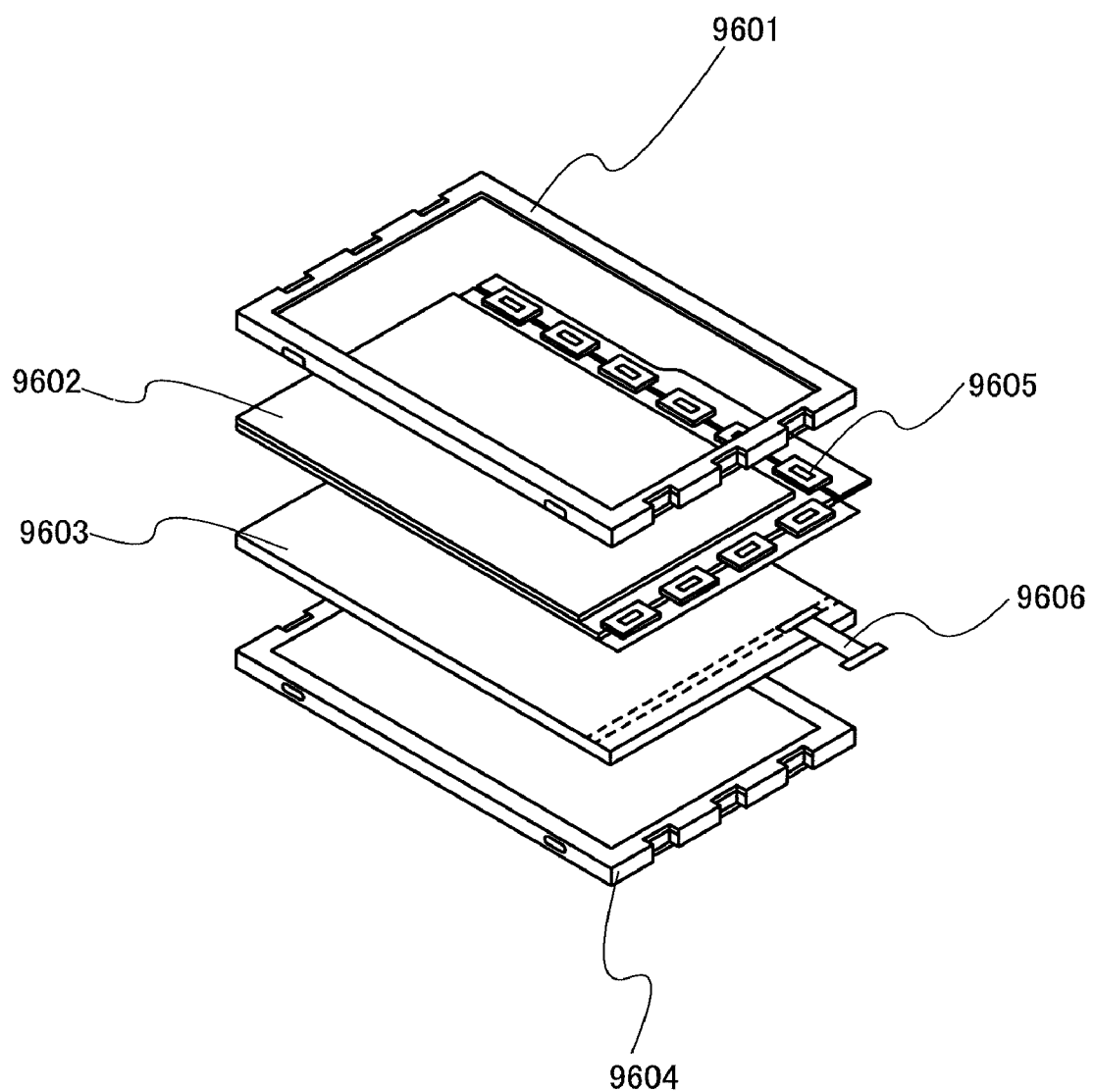
FIG. 6 illustrates an electronic device according to Embodiment.

FIG. 6 illustrates an example of a liquid crystal display device using the light-emitting device of an embodiment of the present invention as a backlight. The liquid crystal display device illustrated in FIG. 6 includes a housing 9601, a liquid crystal layer 9602, a backlight 9603, and a housing 9604, and the liquid crystal layer 9602 is connected to a driver IC 9605. The light-emitting device of an embodiment of the present invention is used as the backlight 9603, and current is supplied through a terminal 9606.

The light-emitting device of an embodiment of the present invention is used as the backlight of the liquid crystal display device, whereby a backlight having high emission efficiency and reduced power consumption can be provided. In addition, the light-emitting device of an embodiment of the present invention is a plane-emission lighting system and can have a larger area. Therefore, the backlight can also have a larger area, which enables the liquid crystal display device to have a larger area. Moreover, since the light-emitting device of an embodiment of the present invention is thin and consumes less power, reduction in the thickness and power consumption of a display device can also be achieved. Furthermore, since the light-emitting device of an embodiment of the present invention is capable of light emission with high luminance, a liquid crystal display device using the light-emitting device of an embodiment of the present invention is also capable of light emission with high luminance.

Figure 7:
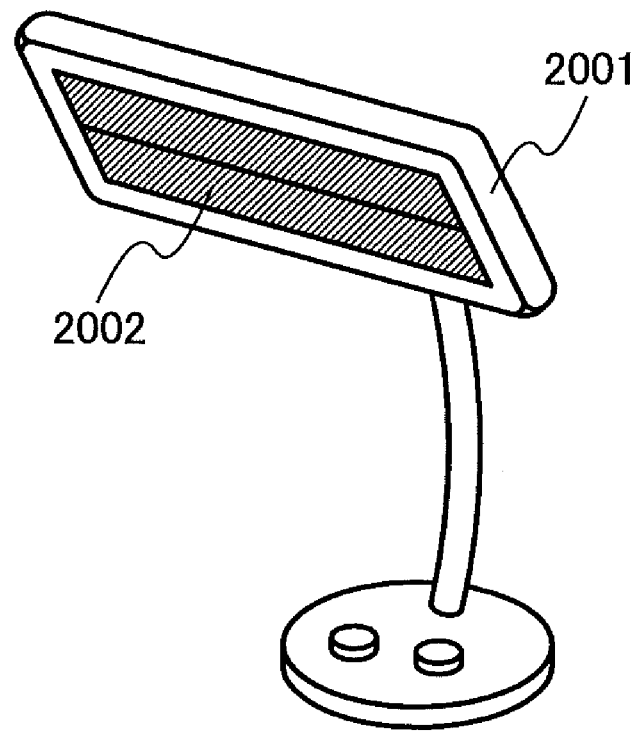
FIG. 7 illustrates a lighting system according to Embodiment.

FIG. 7 illustrates an example in which the light-emitting device to which an embodiment of the present invention is applied is used as a desk lamp that is a lighting system. The desk lamp illustrated in FIG. 7 includes a chassis 2001 and a light source 2002, and the light-emitting device of an embodiment of the present invention is used as the light source 2002. The light-emitting device of an embodiment of the present invention achieves high emission efficiency, capability of long-time driving, and low power consumption, and thus the table lamp also achieves high emission efficiency, capability of long-time driving, and low power consumption.

Figure 8:
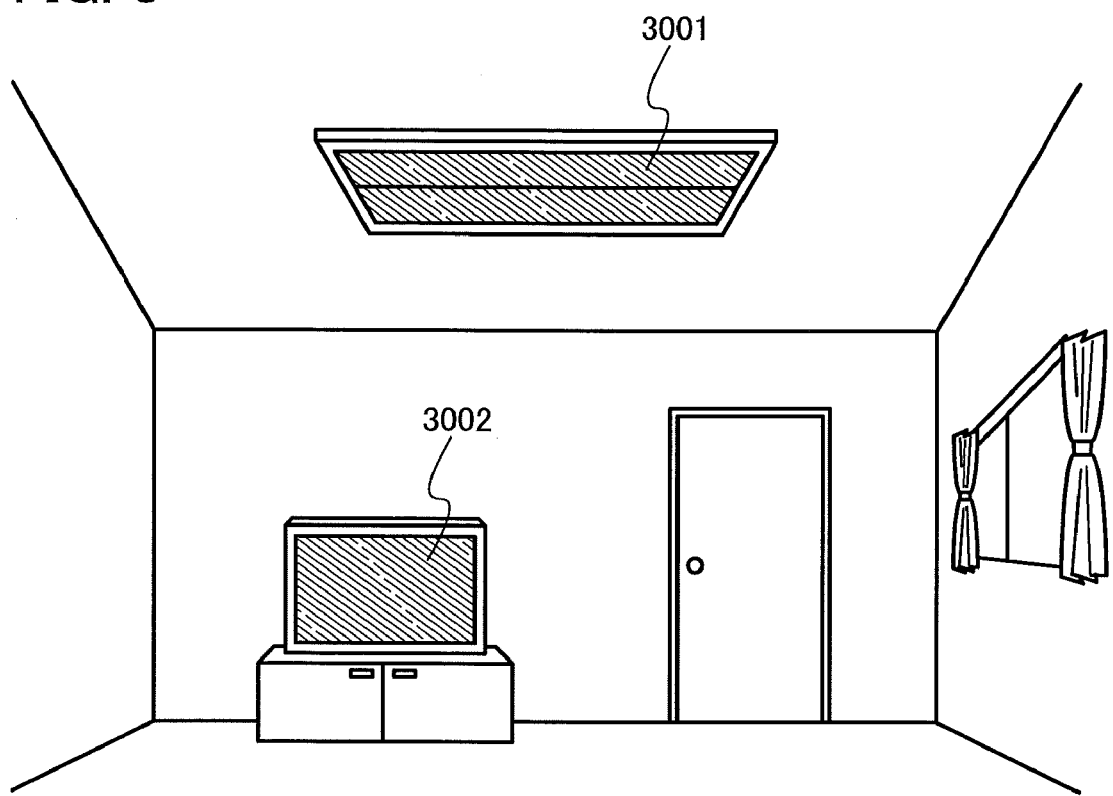
FIG. 8 illustrates a lighting system according to Embodiment.

FIG. 8 illustrates an example in which the light-emitting device to which an embodiment of the present invention is applied is used as an indoor lighting system 3001.

Since the light-emitting device of an embodiment of the present invention can also have a larger area, the light-emitting device of an embodiment of the present invention can be used as a lighting system having a large area. In addition, since the light-emitting device of an embodiment of the present invention is thin and consumes less power, it can be used as a thin lighting system with low power consumption. In a room where the light-emitting device to which an embodiment of the present invention is thus applied is used as the indoor lighting system 3001, a television set 3002 according to an embodiment of the present invention illustrated in FIG. 5A is placed, whereby public broadcasting and movies can be watched. In such a case, since both of the devices consume less power, powerful images can be watched in a bright room without concern about electricity bill.

EXAMPLE 1

SYNTHESIS EXAMPLE 1

In Example 1, a synthesis method of 3-(4-(3,5-diphenyl-4H-1,2,4-triazol-4-yl)phenyl)pyridine (Py-TAZ) which is a triarylamine derivative described as the structural formula (1) in Embodiment 1 will be described.

[Chemical Formula 17]

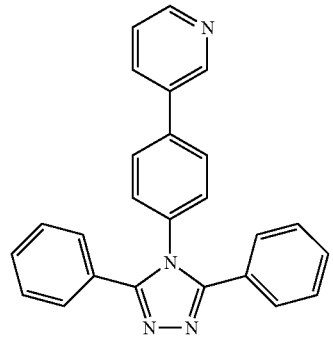

(1)

Step 1: Synthesis of Benzohydrazide

A synthesis scheme of benzohydrazide is shown in (b-1).

[Chemical Formula 18]

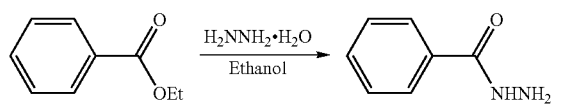

(b-1)

Into a 200 mL three-neck flask was put 25 g (0.17 mol) of ethyl benzoate, and 60 mL of ethanol was added thereto, and the mixture was stirred. After that, 20 mL of hydrazine monohydrate was added, and the mixture was stirred at 78° C. for 8 hours while being heated. After the reaction, the reactive solution was added to about 500 mL of water, and ethyl acetate was added to the solution for extraction. The organic layer and an aqueous layer were separated, and the organic layer was washed with a saturated sodium hydrogen carbonate solution and saturated saline, in the order given. Magnesium sulfate was added to the organic layer to dry the organic layer. This mixture was subjected to suction filtration to remove magnesium sulfate, whereby the filtrate was obtained. The obtained filtrate was concentrated to give a solid. The obtained solid was recrystallized with a mixed solvent of ethanol and hexane to give 15 g of a white solid of benzohydrazide, which was the object of the synthesis, at a yield of 66%.

Step 2: Synthesis of 1,2-dibenzoylhydrazine

A synthesis scheme of 1,2-dibenzoylhydrazine is shown in (b-2).

[Chemical Formula 19]

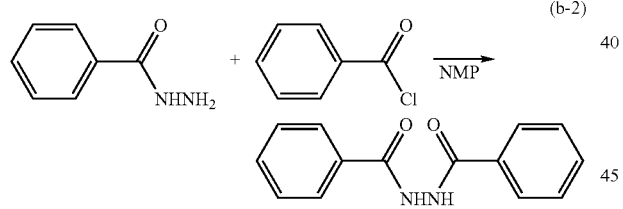

(b-2)

Into a 300 mL three-neck flask was put 10 g (73 mmol) of benzohydrazide, and 25 mL of N-methyl-2-pyrrolidone was added thereto, and the mixture was stirred. After that, a mixed solution of 10 mL of N-methyl-2-pyrrolidone and 10 mL (88 mmol) of benzoyl chloride was dripped into the mixture through a 50 mL dropping funnel. This mixture was stirred at 80° C. for 3 hours, and the contents of the flask were reacted. After the reaction, the reaction solution was added to about 500 mL of water and the mixture was stirred, so that a solid was precipitated. The precipitated solid was collected by suction filtration. The collected solid was washed with water, and methanol was added to the obtained solid so that the solid was washed to give 10 g of a powdery white solid of 1,2-dibenzoylhydrazine, which was the object of the synthesis, at a yield of 57%.

Step 3: Synthesis of 1,2-bis[chloro(phenyl)methylidene]hydrazone

A synthesis scheme of 1,2-bis[chloro(phenyl)methylidene]hydrazone is shown in (b-3).

[Chemical Formula 20]

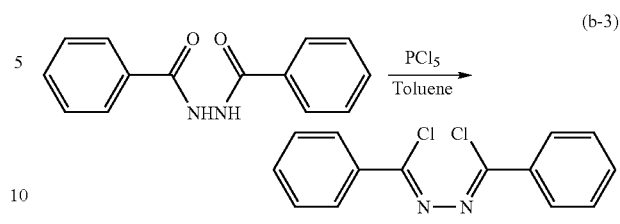

(b-3)

Into a 200 mL three-neck flask were put 5.0 g (21 mmol) of 1,2-dibenzoylhydrazine and 9.5 g (46 mmol) of phosphorus pentachloride, and 80 mL of toluene was added to the mixture. The mixture was stirred at 120° C. for 3 hours, and the contents of the flask were reacted. After the reaction, the reactive solution was added to about 100 mL of water and the mixture was stirred. An organic layer and an aqueous layer were separated, and the organic layer was washed with water and a saturated sodium hydrogen carbonate solution. Magnesium sulfate was added to the organic layer to dry the organic layer. This mixture was subjected to suction filtration to remove magnesium sulfate, whereby the filtrate was obtained. The obtained filtrate was concentrated to give a solid. The obtained solid was washed with methanol to give 4.9 g of a powdery light yellow solid of 1,2-bis[chloro(phenyl)methylidene]hydrazone, which was the object of the synthesis, at a yield of 85%.

Step 4: Synthesis of 4-(4-bromophenyl)-3,5-diphenyl-4H-1,2,4-triazole

A synthesis scheme of 4-(4-bromophenyl)-3,5-diphenyl-4H-1,2,4-triazole is shown in (b-4).

[Chemical Formula 21]

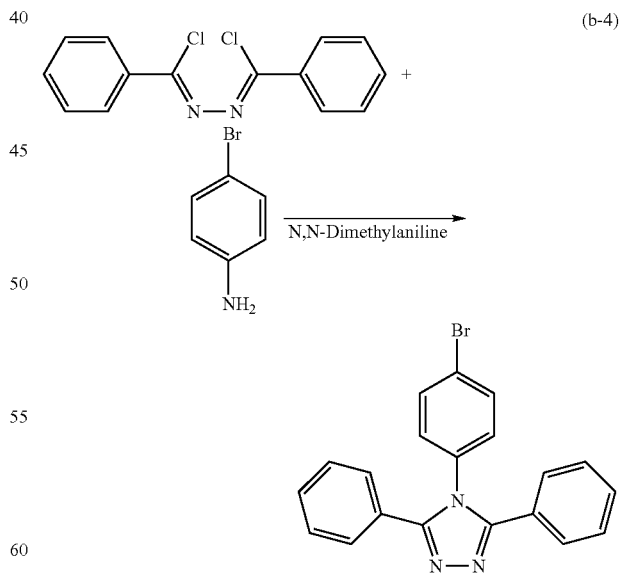

(b-4)

Into a 100 mL three-neck flask were put 4.5 g (16 mmol) of 1,2-bis[chloro(phenyl)methylidene]hydrazone, 2.0 g (16 mmol) of 4-bromoaniline, and 30 mL of N,N-dimethylaniline, and the air in the flask was replaced with nitrogen. The mixture was stirred at 135° C. for 5 hours. After the reaction, the reaction solution was added to about 100 mL of 1 M diluted hydrochloric acid, and the mixture was stirred for 30 minutes, whereby a solid was precipitated. The precipitated solid was subjected to suction filtration to give a solid. The obtained solid was dissolved in toluene and washed with water and a saturated sodium carbonate solution. Magnesium sulfate was added to the organic layer to dry the organic layer. The mixture was subjected to suction filtration to remove magnesium sulfate, whereby the filtrate was obtained. The obtained filtrate was concentrated to give a solid. The obtained solid was recrystallized with a mixed solvent of ethanol and hexane to give 2.3 g of a powdery white solid of 4-(4-bromophenyl)-3,5-diphenyl-4H-1,2,4-triazole, which was the object of the synthesis, at a yield of 38%.

Step 5: Synthesis of 3-(4-(3,5-diphenyl-4H-1,2,4-triazol-4-yl)phenyl)pyridine (Py-TAZ)

A synthesis scheme of 3-(4-(3,5-diphenyl-4H-1,2,4-triazol-4-yl)phenyl)pyridine (Py-TAZ) is shown in (b-5).

[Chemical Formula 22]

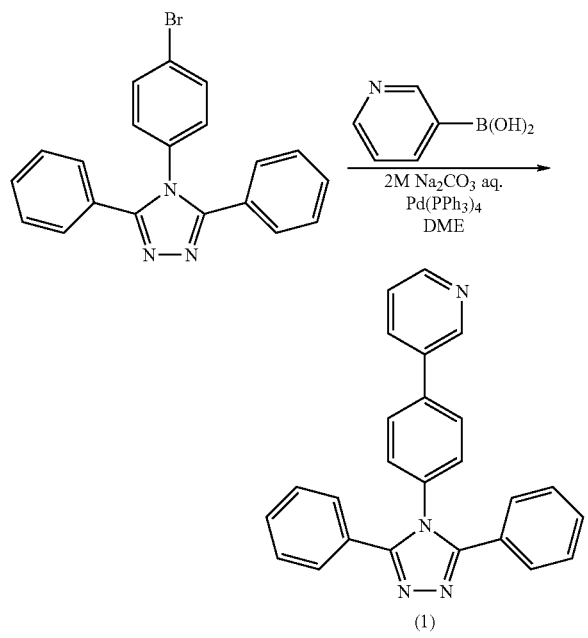

(b-5)

(1)

Into a 100 mL three-neck flask were put 2.0 g (5.3 mmol) of 4-(4-bromophenyl)-3,5-diphenyl-4H-1,2,4-triazole, 0.98 g (8.0 mmol) of 3-pyridineboronic acid, and 0.28 g (1.1 mmol) of tetrakis(triphenylphosphine)palladium(0), and 10 mL of 1,2-dimethoxyethane (DME) and 10 mL of a 2M sodium carbonate aqueous solution were added to the mixture. This mixture was degassed under reduced pressure. After that, the air in the flask was replaced with nitrogen. This mixture was stirred at 95° C. for 3 hours. After the stir, dichloromethane was added to the reacted mixture, and the suspension was washed with 1M diluted hydrochloric acid, a saturated sodium hydrogen carbonate solution, and saturated saline. The organic layer and the aqueous layer were separated. Magnesium sulfate was added to the organic layer to dry the organic layer. After the drying, this mixture was subjected to suction filtration through Celite (Catalog No. 531-16855, manufactured by Wako Pure Chemical Industries, Ltd.) to obtain the filtrate. The obtained filtrate was concentrated and purified by silica gel column chromatography. For the column chromatography, first toluene and then a mixed solvent of toluene and ethyl acetate (toluene:ethyl acetate=1:3) were used as developing solvents. The obtained fraction was concentrated to give a solid. The obtained solid was recrystallized with a mixed solvent of ethanol and hexane to give 1.5 g of a powdery white solid, which was the object of the synthesis, at a yield of 76%.

Sublimation purification of 0.75 g of the obtained white solid was performed by train sublimation. The sublimation purification was performed at a reduced pressure of 7.0 Pa, with the argon flow rate of 4 mL/min, at 205° C. for 15 hours. 0.60 g of the white solid was obtained at a yield of 80%.

Figure 9A:
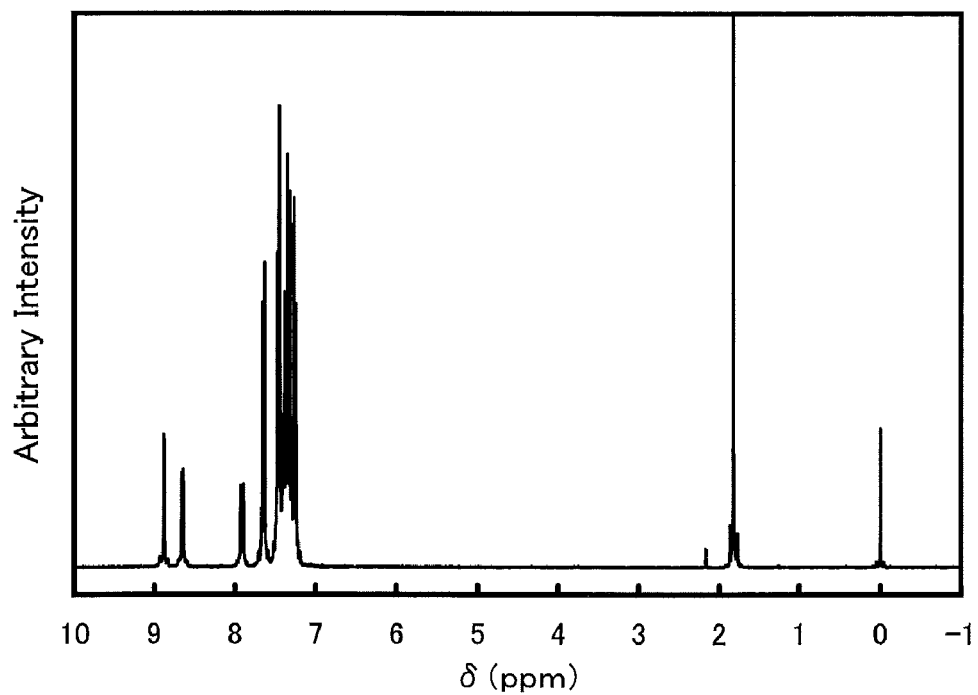
FIGS. 9A and 9B are $^1$H NMR charts of 3-(4-(3,5-diphenyl-4H-1,2,4-triazol-4-yl)phenyl)pyridine (Py-TAZ) synthesized in Example 1.
Figure 9B:
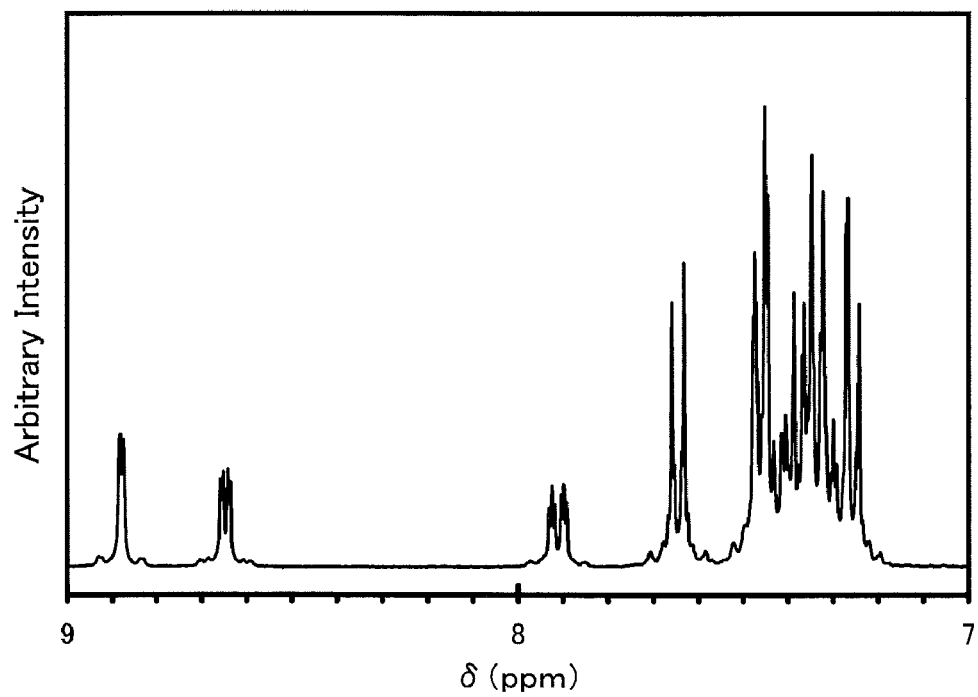

The result of an analysis by nuclear magnetic resonance spectrometry ($^1$H-NMR) of the powder obtained in above Step 5 is shown below. Further, $^1$H-NMR charts are shown in FIGS. 9A and 9B. According to the analysis result of $^1$H-NMR, 3-(4-(3,5-diphenyl-4H-1,2,4-triazol-4-yl)phenyl)pyridine (Py-TAZ) of an embodiment of the present invention, which is represented by the above structural formula (1), was obtained in Example 1.

$^1$H NMR. δ (CDCl$_3$, 300 MHz): δ=7.22-7.49 (m, 13H), 7.64 (d, J=8.3 Hz, 2H), 7.91 (dt, J$_1$=8.3 Hz, J$_2$=2.0 Hz, 1H), 8.64 (dd, J$_1$=4.9 Hz, J$_2$=2.0 Hz, 1H), 8.88 (sd, J=2.0 Hz, 1H).

Next, the ultraviolet-visible absorption spectrum and the emission spectrum of Py-TAZ were measured. A toluene solution including Py-TAZ in a quartz cell and a Py-TAZ thin film vacuum-evaporated onto a quartz substrate were used as samples. The absorption spectrum was measured with an ultraviolet-visible spectrophotometer (V-550, manufactured by JASCO Corporation).

Figure 10A:
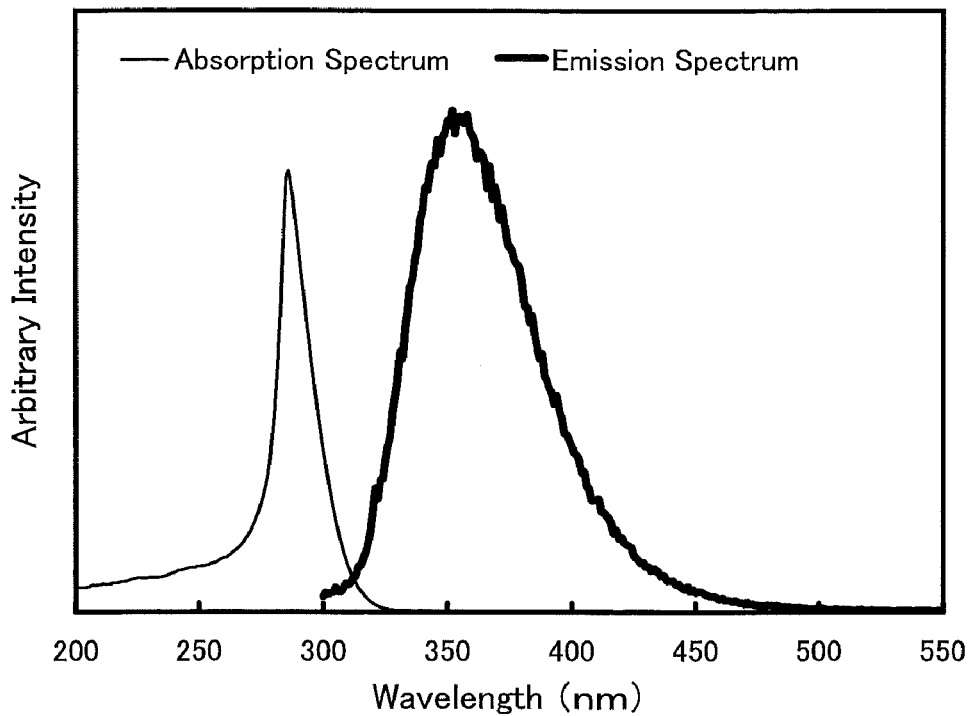
FIGS. 10A and 10B are graphs showing ultraviolet-visible absorption spectra and emission spectra of 3-(4-(3,5-diphenyl-4H-1,2,4-triazol-4-yl)phenyl)pyridine (Py-TAZ), which is synthesized in Example 1, included in a toluene solution and a thin film.
Figure 10B:
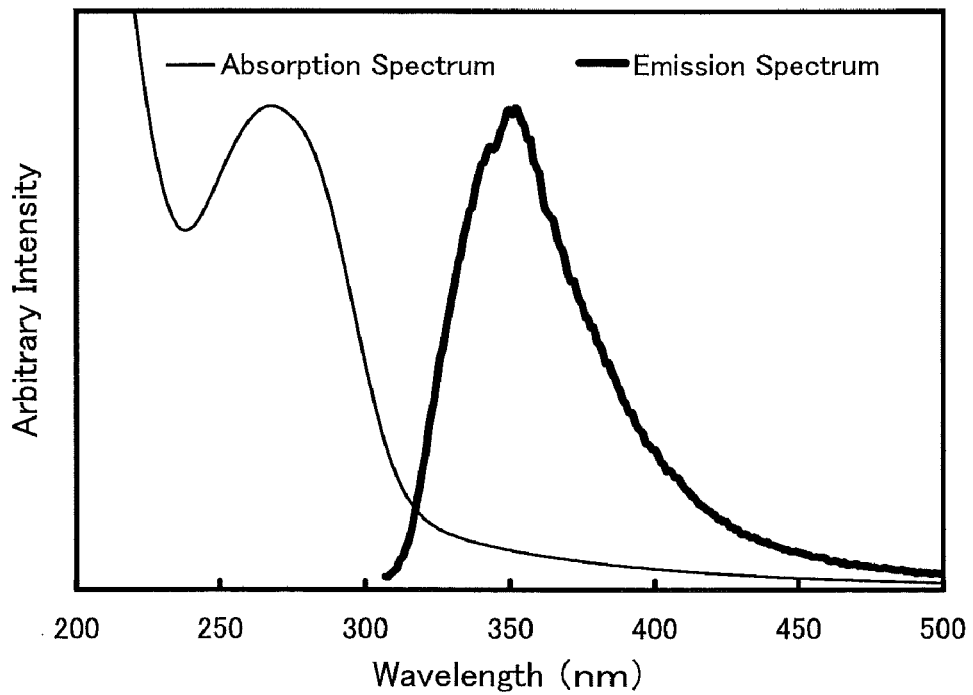

FIG. 10A shows the measurement result of Py-TAZ included in the toluene solution and FIG. 10B shows the measurement result of the Py-TAZ thin film. The horizontal axis represents wavelength (nm) and the vertical axis represents arbitrary intensity of absorbance and emission intensity. As for the absorption spectrum in the case where the sample was the solution, the result obtained by subtraction of the absorption spectrum of the quartz cell including only toluene is shown. In addition, as for the absorption spectrum in the case where the sample was the thin film, the result obtained by subtraction of the absorption spectrum of the quartz substrate is shown.

The peak wavelength of the absorption spectrum of Py-TAZ included in the toluene solution was 285 nm and the peak wavelength of the fluorescent spectrum was 356 nm (excitation wavelength: 292 nm). The peak wavelength of the absorption spectrum of the Py-TAZ thin film was 268 nm and the peak wavelength of the fluorescent spectrum was 351 nm (excitation wavelength: 274 nm). Accordingly, it was found that Py-TAZ is a substance which has a large energy gap.

Moreover, the result of the ionized potential of Py-TAZ in the thin film state measured by a photoelectron spectrometer (AC-2 photoelectron spectrometer manufactured by Riken Keiki, Co., Ltd.) in the atmosphere was 5.58 eV. Accordingly, the HOMO level was found to be −5.58 eV. Furthermore, the absorption edge was obtained by tauc plot assuming direct transition with the absorption spectrum data of the Py-TAZ thin film. When the absorption edge was estimated as an optical energy gap, the energy gap was 4.01 eV. Therefore, a LUMO level of −1.57 eV was obtained from the obtained values of the energy gap and the HOMO level.

EXAMPLE 2

Figure 11:
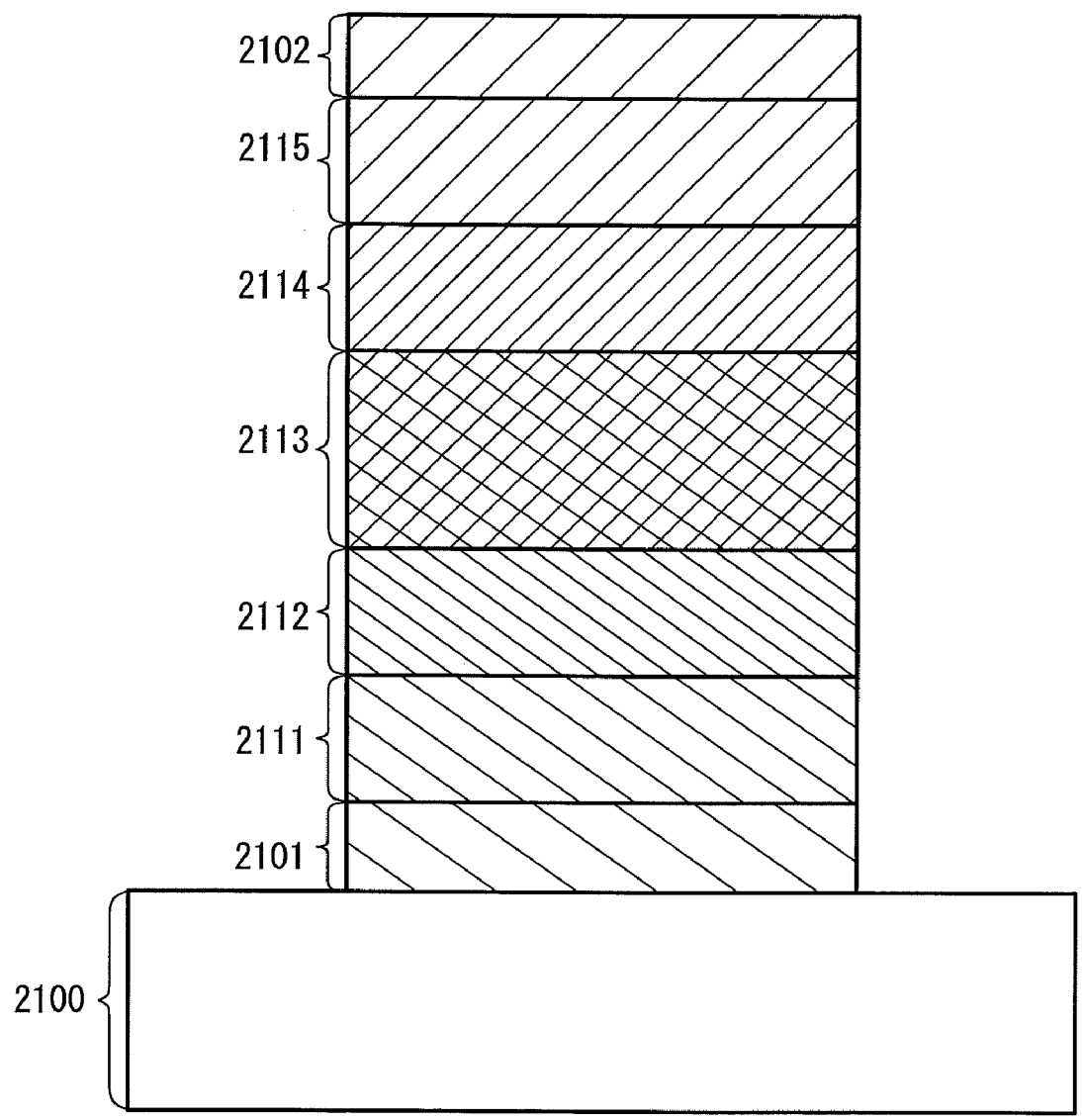
FIG. 11 illustrates a light-emitting element manufactured in Example 2.

In Example 2, light-emitting elements of embodiments of the present invention will be described with reference to FIG. 11. Structural formulae of materials used in Example 2 are shown below.

[Chemical Formula 23]

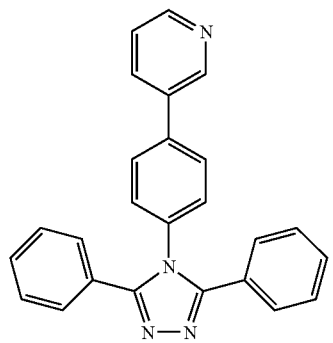

(1)

Hereinafter, a method for manufacturing the light-emitting element of Example 2 will be described.

(Light-emitting Element 1)

First, indium tin oxide containing silicon oxide (ITSO) was deposited over a glass substrate 2100 by a sputtering method to form a first electrode 2101. The thickness of the first electrode was 110 nm and the area thereof was 2 mm×2 mm.

Next, the substrate provided with the first electrode 2101 was fixed to a substrate holder provided in a vacuum evaporation apparatus so that a surface on which the first electrode 2101 was formed faced downward. After the pressure in the vacuum evaporation apparatus was reduced to approximately $10^{-4}$ Pa, a layer 2111 containing a composite material of an organic compound and an inorganic compound was formed on the first electrode 2101 by co-evaporation of 4,4'-bis[N-(1-naphthyl)-N-phenylamino]biphenyl (NPB) and molybdenum(VI) oxide. The thickness of the layer 2111 was 40 nm and the weight ratio of NPB to molybdenum(VI) oxide was adjusted to 4:1 (=NPB:molybdenum oxide). Note that the co-evaporation is an evaporation method in which evaporation is performed at the same time from a plurality of evaporation sources in one treatment chamber.

Next, 4,4',4''-tris(carbazol-9-yl)triphenylamine (TCTA) was deposited to a thickness of 10 nm on the layer 2111 containing a composite material by an evaporation method using resistance heating to form a hole-transporting layer 2112.

In addition, 3-(4-(3,5-diphenyl-4H-1,2,4-triazol-4-yl)phenyl)pyridine (Py-TAZ) which is represented by the structural formula (1) and bis[2-(4',6'-difluorophenyl)pyridinato-N, C²']iridium(III)picolinate (FIrpic) were co-evaporated to form a light-emitting layer 2113 with a thickness of 30 nm on the hole-transporting layer 2112. Here, the weight ratio of Py-TAZ to FIrpic was adjusted to 1:0.05 (=Py-TAZ:FIrpic).

After that, 3-(4-biphenylyl)-4-phenyl-5-(4-tert-butylphenyl)-1,2,4-triazole (TAZ01) was deposited to a thickness of 10 nm on the light-emitting layer 2113 by an evaporation method using resistance heating to form an electron-transporting layer 2114.

Furthermore, bathophenanthroline (BPhen) and lithium were co-evaporated on the electron-transporting layer 2114 to form an electron-injecting layer 2115 with a thickness of 20 nm. Here, the weight ratio of BPhen to lithium was adjusted to 1:0.01 (=BPhen:lithium).

Finally, aluminum was deposited to a thickness of 200 nm on the electron-injecting layer 2115 by an evaporation method using resistance heating to form a second electrode 2102. Accordingly, a light-emitting element 1 was manufactured.

(Light-emitting Element 2)

A second light-emitting element 2 was manufactured in a similar manner to the light-emitting element 1 except that the electron-transporting layer 2114 was formed using, instead of TAZ01, 3-(4-(3,5-diphenyl-4H-1,2,4-triazol-4-yl)phenyl)pyridine (Py-TAZ) which is represented by the structural formula (1) over the same substrate over which the light-emitting element 1 was manufactured.

In other words, 3-(4-(3,5-diphenyl-4H-1,2,4-triazol-4-yl)phenyl)pyridine (Py-TAZ) was deposited to a thickness of 10 nm over the light-emitting layer 2113 by an evaporation method using resistance heating to form the electron-transporting layer 2114. The layers other than the electron-transporting layer 2114 were formed in a manner similar to those of the light-emitting element 1.

The light-emitting elements 1 and 2 obtained through the above steps were sealed in a glove box under a nitrogen atmosphere without being exposed to atmospheric air. Then, the operating characteristics of the light-emitting elements were measured. The measurement was performed at a room temperature (in the atmosphere where the temperature was kept at 25° C.).

Figure 12:
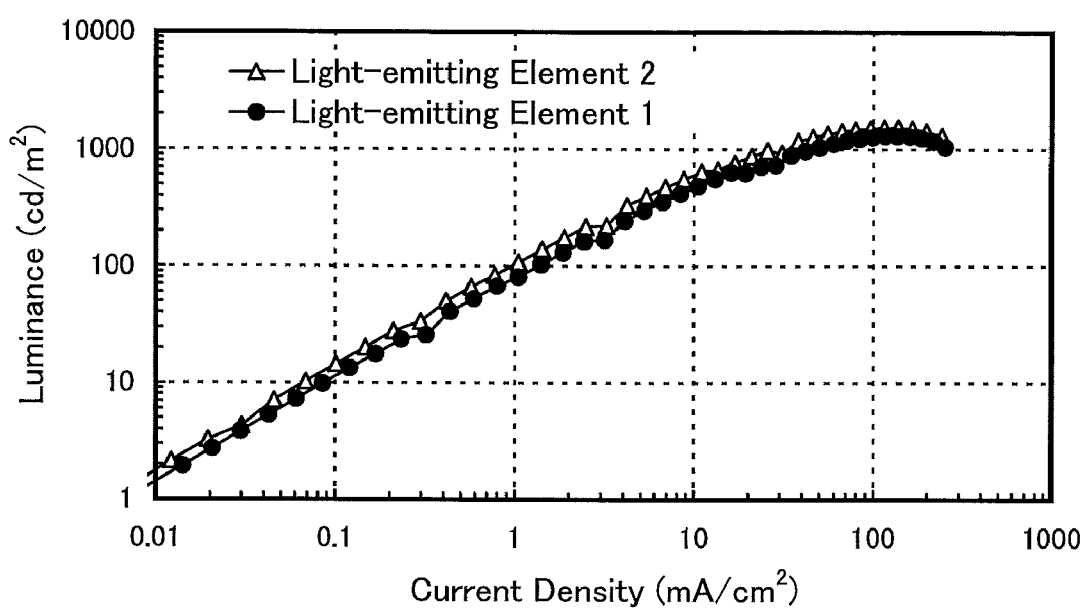
FIG. 12 is a graph showing current density-luminance characteristics of the light-emitting element manufactured in Example 2.
Figure 13:
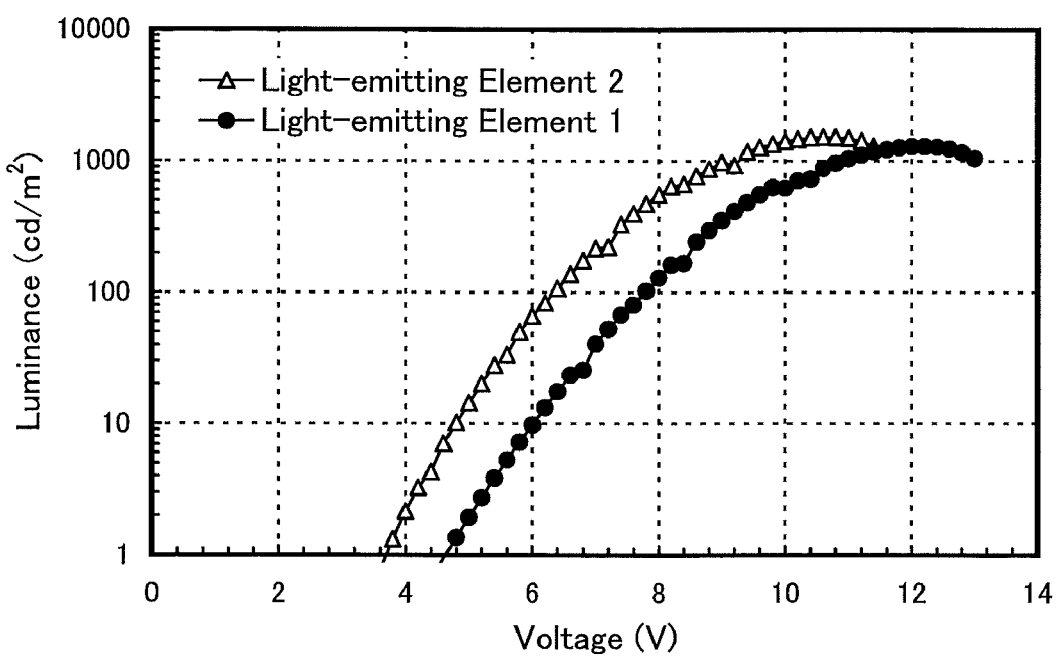
FIG. 13 is a graph showing voltage-luminance characteristics of the light-emitting element manufactured in Example 2.
Figure 14:
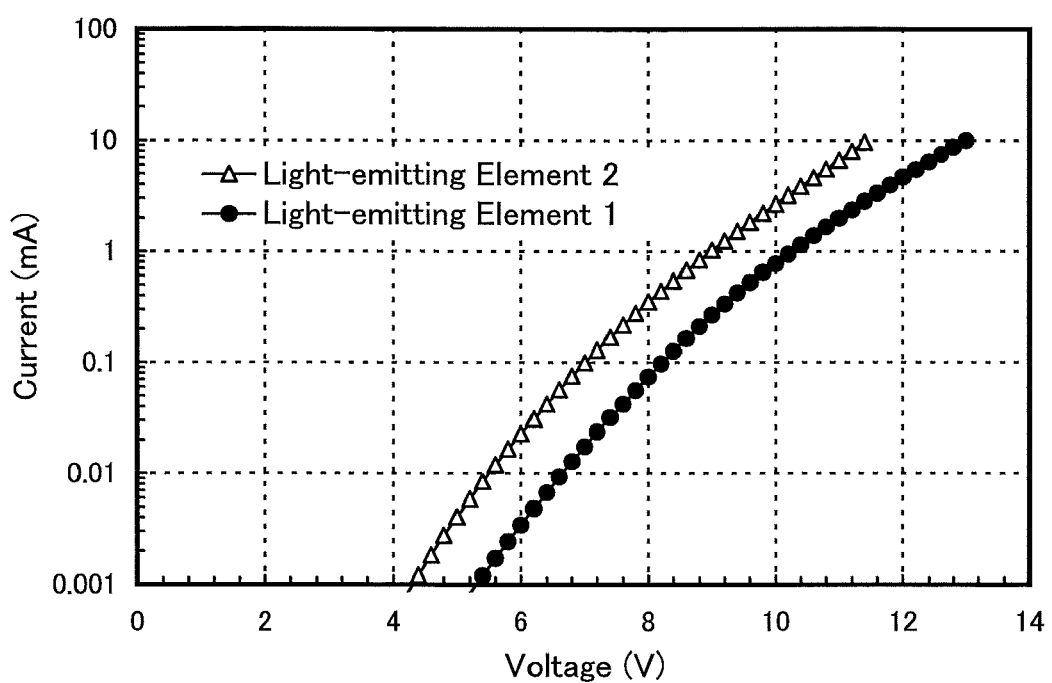
FIG. 14 is a graph showing voltage-current characteristics of the light-emitting element manufactured in Example 2.

FIG. 12 shows the current density-luminance characteristics of the light-emitting elements 1 and 2. FIG. 13 shows the voltage-luminance characteristics thereof. FIG. 14 shows the voltage-current characteristics thereof.

As for the light-emitting element 1, CIE color coordinates at a luminance of 10 cd/m² are x=0.19 and y=0.36, the current efficiency is 11 cd/A, and the external quantum efficiency is 5.6%. Light-blue light emission derived from FIrpic was efficiently obtained.

As for the light-emitting element 2, CIE color coordinates at a luminance of 10 cd/m² are x=0.19 and y=0.37, the current efficiency is 15 cd/A, and the external quantum efficiency is 7.2%. Light-blue light emission derived from FIrpic was efficiently obtained.

As described above, in the light-emitting elements of Example 2, FIrpic which exhibits blue and blue-tinged light emission of a short wavelength emits light efficiently, which shows that Py-TAZ of an embodiment of the present invention has high triplet excitation energy and exhibits excellent characteristics as a host material of a phosphorescent compound which exhibits blue and blue-tinged light emission.

Further, in the voltage-luminance characteristics (FIG. 13), the light-emitting element 2 of Example 2 achieved higher luminance at lower voltage than the light-emitting element 1 of Example 2. Similarly, in the voltage-current characteristics (FIG. 14), higher current can flow in the light-emitting element 2 of Example 2 than in the light-emitting element 1 of Example 2. This is considered to result from the difference of the electron-transporting layers between the light-emitting elements 1 and 2.

In other words, it can be said that Py-TAZ of an embodiment of the present invention which is used for the electron-transporting layer of the light-emitting element 2 is superior in an electron-transporting property to TAZ01 which is used for the electron-transporting layer of the light-emitting element 1. Accordingly, Py-TAZ of an embodiment of the present invention was found to be useful also as an electron-transporting material to be used for the electron-transporting layer.

By application of an embodiment of the present invention, FIrpic which is a phosphorescent compound which exhibits light emission of a short wavelength can be efficiently emitted at low voltage. In other words, a light-emitting element which efficiently emits light of a short wavelength at low voltage can be provided.

This application is based on Japanese Patent Application serial no. 2008-223655 filed with Japan Patent Office on Sep. 1, 2008, the entire contents of which are hereby incorporated by reference.

What is claimed is:

1. A triazole derivative represented by the formula (G1):

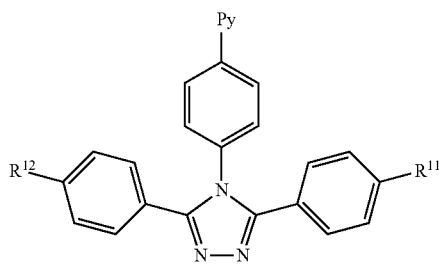

wherein Py represents any of a 2-pyridyl group, a 3-pyridyl group, or a 4-pyridyl group, and wherein $R^{11}$ and $R^{12}$ each represent any of hydrogen, an alkyl group having 1 to 4 carbon atoms, an alkoxy group having 1 to 4 carbon atoms, or a phenyl group.

2. A triazole derivative represented by the formula (G2):

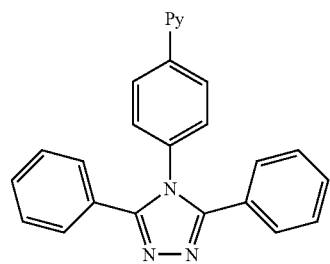

wherein Py represents any of a 2-pyridyl group, a 3-pyridyl group, or a 4-pyridyl group.

3. A triazole derivative represented by the structural formula (1):

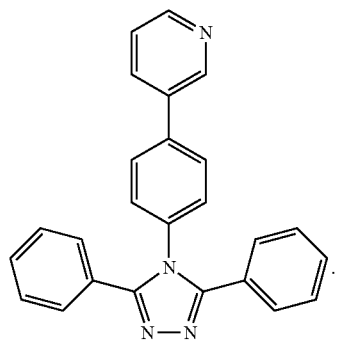

4. A light-emitting element comprising:
a pair of electrodes;
a triazole derivative represented by the formula (G1) between the pair of electrodes:

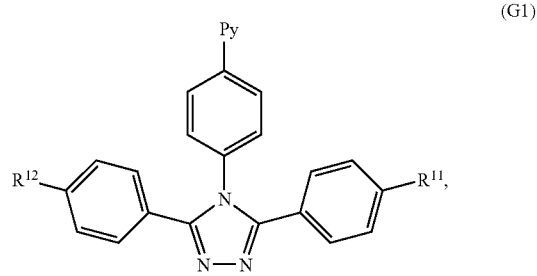

wherein Py represents any of a 2-pyridyl group, a 3-pyridyl group, or a 4-pyridyl group; and wherein $R^{11}$ and $R^{12}$ each represent any of hydrogen, an alkyl group having 1 to 4 carbon atoms, an alkoxy group having 1 to 4 carbon atoms, or a phenyl group.

5. The light-emitting element according to claim 4 further comprising:
a substance emitting phosphorescence,
wherein the triazole derivative and the substance emitting phosphorescence are contained in a light-emitting layer between the pair of electrodes.

6. The light-emitting element according to claim 4 further comprising:
a light-emitting layer containing a light-emitting substance between the pair of electrodes,
wherein one of the pair of electrodes is an anode, and another of the pair of electrodes is a cathode,
wherein a layer containing the triazole derivative is provided between the light-emitting layer and the cathode so as to be in contact with the light-emitting layer.

7. The light-emitting element according to claim 4 further comprising:
a substance emitting phosphorescence,
wherein one of the pair of electrodes is an anode, and another of the pair of electrodes is a cathode,
wherein the triazole derivative and the substance emitting phosphorescence are contained in a light-emitting layer between the cathode and the anode,
wherein a layer containing the triazole derivative is provided between the light-emitting layer and the cathode so as to be in contact with the light-emitting layer.

8. A light-emitting device comprising:
the light-emitting element according to claim 4; and
a control unit controlling emission of the light-emitting element.

9. An electronic device comprising:
the light-emitting element according to claim 4; and
a display portion provided with a control unit controlling emission of the light-emitting element.

10. A light-emitting element comprising:
a pair of electrodes;
a triazole derivative represented by the formula (G2) between the pair of electrodes:

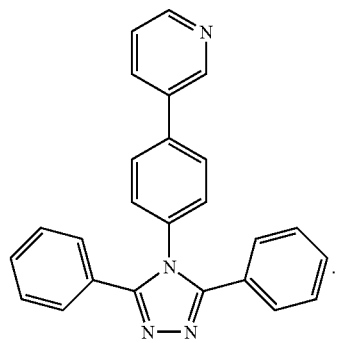

(G2)

wherein Py represents any of a 2-pyridyl group, a 3-pyridyl group, or a 4-pyridyl group.

11. The light-emitting element according to claim 10 further comprising:
a substance emitting phosphorescence,
wherein the triazole derivative and the substance emitting phosphorescence are contained in a light-emitting layer between the pair of electrodes.

12. The light-emitting element according to claim 10 further comprising:
a light-emitting layer containing a light-emitting substance between the pair of electrodes,
wherein one of the pair of electrodes is an anode, and another of the pair of electrodes is a cathode,
wherein a layer containing the triazole derivative is provided between the light-emitting layer and the cathode so as to be in contact with the light-emitting layer.

13. The light-emitting element according to claim 10 further comprising:
a substance emitting phosphorescence,
wherein one of the pair of electrodes is an anode, and another of the pair of electrodes is a cathode,
wherein the triazole derivative and the substance emitting phosphorescence are contained in a light-emitting layer between the cathode and the anode,
wherein a layer containing the triazole derivative is provided between the light-emitting layer and the cathode so as to be in contact with the light-emitting layer.

14. A light-emitting device comprising:
the light-emitting element according to claim 10; and
a control unit controlling emission of the light-emitting element.

15. An electronic device comprising:
the light-emitting element according to claim 10; and
a display portion provided with a control unit controlling emission of the light-emitting element.

16. A light-emitting element comprising:
a pair of electrodes;
a triazole derivative represented by the structural formula (1) between the pair of electrodes:

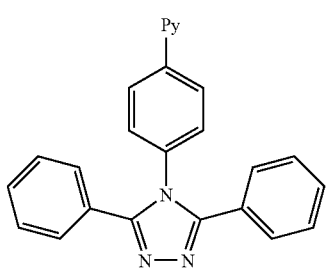

(1)

17. The light-emitting element according to claim 16 further comprising:
a substance emitting phosphorescence,
wherein the triazole derivative and the substance emitting phosphorescence are contained in a light-emitting layer between the pair of electrodes.

18. The light-emitting element according to claim 16 further comprising:
a light-emitting layer containing a light-emitting substance between the pair of electrodes,
wherein one of the pair of electrodes is an anode, and another of the pair of electrodes is a cathode,
wherein a layer containing the triazole derivative is provided between the light-emitting layer and the cathode so as to be in contact with the light-emitting layer.

19. The light-emitting element according to claim 16 further comprising:
a substance emitting phosphorescence,
wherein one of the pair of electrodes is an anode, and another of the pair of electrodes is a cathode,
wherein the triazole derivative and the substance emitting phosphorescence are contained in a light-emitting layer between the cathode and the anode,
wherein a layer containing the triazole derivative is provided between the light-emitting layer and the cathode so as to be in contact with the light-emitting layer.

20. A light-emitting device comprising:
the light-emitting element according to claim 16; and
a control unit controlling emission of the light-emitting element.

21. An electronic device comprising:
the light-emitting element according to claim 16; and
a display portion provided with a control unit controlling emission of the light-emitting element.

* * * * *